United States Patent [19]

Kawamura et al.

[11] Patent Number: 5,317,021
[45] Date of Patent: May 31, 1994

[54] 3-MERCAPTO-GLUTAMIC ACID DERIVATIVES

[75] Inventors: Masanori Kawamura; Yoshinobu Arai; Hideki Aishita, all of Osaka, Japan

[73] Assignee: ONO Pharmaceutical Co., Ltd., Osaka, Japan

[21] Appl. No.: 971,229

[22] Filed: Nov. 4, 1992

Related U.S. Application Data

[62] Division of Ser. No. 679,214, Apr. 2, 1991, Pat. No. 5,202,340, which is a division of Ser. No. 347,673, May 5, 1989, Pat. No. 5,017,589.

[30] Foreign Application Priority Data

May 6, 1988 [JP] Japan .................................. 63-109191
Oct. 3, 1988 [JP] Japan .................................. 63-249433

[51] Int. Cl.$^5$ ................ A61K 31/505; A61K 31/445; A61K 31/54; C07D 213/56; C07D 239/02; C07D 277/82

[52] U.S. Cl. .................................... 514/275; 514/221; 514/255; 514/352; 514/367; 514/394; 514/447; 514/472; 514/530; 514/531; 514/538; 540/573; 544/322; 544/323; 544/324; 544/325; 544/330; 544/331; 544/332; 544/335; 546/255; 546/304; 546/307; 546/308; 546/309; 546/310; 546/312; 548/222; 548/305.1; 548/307.4; 548/311.1; 548/362.1; 548/365.7; 548/304.7; 548/311.4; 548/332.5; 548/364.4; 548/371.7; 549/69; 549/480; 560/9; 560/10; 560/11; 560/12; 560/13; 560/16; 562/426; 562/427; 562/429; 562/430

[58] Field of Search ................ 540/573; 544/322, 323, 544/324, 325, 330, 331, 332, 335, 336; 548/152, 161, 162, 163, 165, 167, 169, 171, 222, 329, 366, 338, 339; 514/221, 255, 275, 352, 367, 394, 447, 472, 530, 531, 538; 560/9, 10, 11, 12, 13, 16; 562/426, 427, 429, 430; 546/255, 304, 309, 310, 312, 307, 308; 549/69, 480

[56] References Cited

U.S. PATENT DOCUMENTS

4,401,677 8/1983 Greenberg et al. .................. 424/317

FOREIGN PATENT DOCUMENTS

0115997 2/1984 European Pat. Off. .
0136883 4/1985 European Pat. Off. ............ 424/317
2054586 2/1981 United Kingdom ................ 424/317

*Primary Examiner*—Mukund J. Shah
*Assistant Examiner*—Y. N. Gupta
*Attorney, Agent, or Firm*—Stevens, Davis, Miller & Mosher

[57] ABSTRACT

Amino acid compounds of the formula:

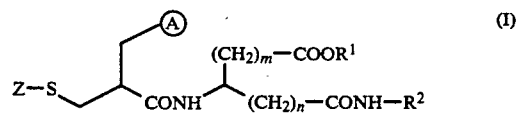

wherein the various symbols are as hereinafter described, which have inhibiting effect on enkephalinase.

28 Claims, No Drawings

3-MERCAPTO-GLUTAMIC ACID DERIVATIVES

This is a division of U.S. Ser. No. 07/679,214, filed Apr. 2, 1991, now U.S. Pat. No. 5,202,340 issued Apr. 13, 1992, which in turn is a division of U.S. Ser. No. 07/347,673, filed May 5, 1989, now U.S. Pat. No. 5,017,589 issued May 21, 1991.

SUMMARY

This invention relates to novel amino acid derivatives having an inhibitory activity on enkephalinase. More particularly, it relates to amino acid derivatives of the general formula:

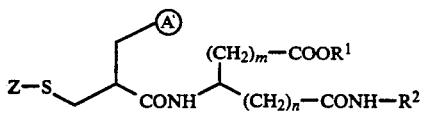

(I)

(wherein the various symbols are as hereinafter described) and non-toxic salts thereof, which have an inhibitory activity on enkephalinase and which are, therefore, useful as analgesic against various pain, the process for the preparation of the derivative of the general formula (I) and enkephalinase inhibitors containing, as active ingredient, the derivative of the general formula (I) or a non-toxic salt thereof.

BACKGROUND

"Enkephalin" is the general term referring to Met[5]-enkephalin (A is Met in the below formula) or Leu[5]-enkephalin (A is Leu in the below formula) of the following formula:

Try-Gly-Gly-Phe-A (wherein A represents Met or Leu). These two pentapeptides bind to opioid receptors and such produces analgic effect. They are neurotransmitters (see Nature, 258, 577 (1975)).

Enkephalinase, found by Malfroy et al, is an enzyme which cleaves Met-enkephalin or Leu-enkephalin at the Gly[3]-Phe[4] bond (see Nature, 276, 523 (1978)). It plays an important role in the termination of an analgic effect which enkephalin has.

Accordingly, it is considered that the inhibition for enkephalinase slows down the deactivation of enkephalin and that the analgic effect maintains.

PRIOR ARTS

Based on the above fact, recent research and development on enkephalinase inhibitors have been actively carried out.

For example, in European Patent Publication No. 38758, the compounds of the general formula:

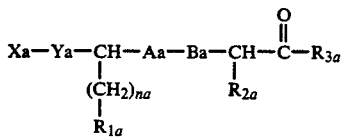

(a)

(wherein
Xa-Ya represents a mercapto group etc.,
na represents zero or one,
Aa-Ba represents a CONH group etc., $R_{1a}$ represents a hydrogen atom, an (substituted) alkyl group, a (substituted) phenyl group etc.,
$R_{2a}$ represents a hydrogen atom, an alkyl group, a phenyl group, a (substituted) benzyl group, a hydroxyalkyl group, an (substituted) alkoxyalkyl group, a phenoxyalkyl group or a mercaptoalkyl group,
$R_{3a}$ represents a group of the formula: $OR_{4a}$ or $N(R_{4a})_2$ and
$R_{4a}$ represents a (substituted) phenyl etc.) are proposed. Especially, thiorphan having the formula:

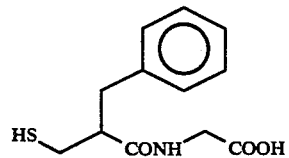

is noted (see Nature, 288, 286 (1980)).

Thereafter, compounds wherein the glycine moiety in thiorphan is replaced by various substituents, have been proposed.

For example, in European Patent Publication No. 136883 (and Japanese Patent Kokai No. 60-136554), the compounds of the general formula:

(b)

(wherein
$R_{1b}$ represents a hydrogen atom or

$R_{2b}$ represents a group of the formula:

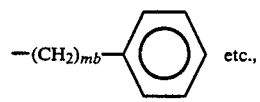 etc., $R_{3b}$ represents a hydrogen atom, an alkyl group, a group of the formula:

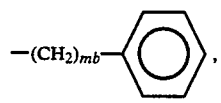,

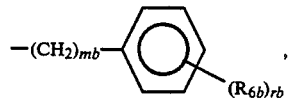,

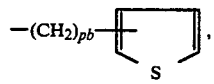,

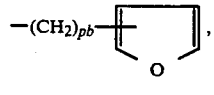,

-continued

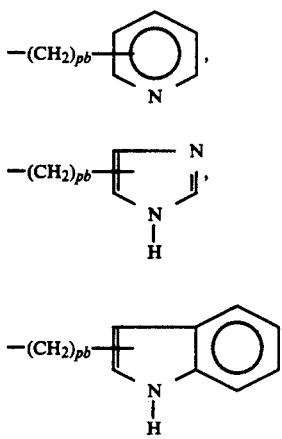

or —(CH$_2$)$_{pb}$-cycloalkyl,

R$_{4b}$ represents a hydroxy group, an alkoxy group, a group of the formula:

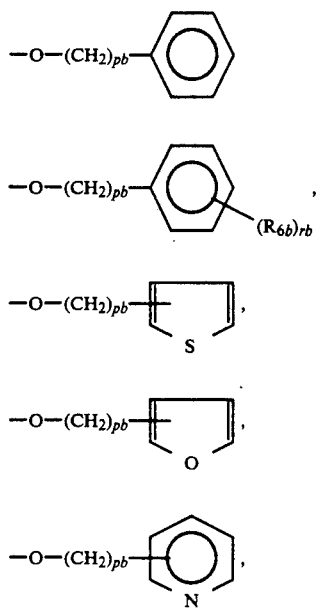

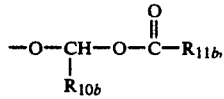

—O—(CH$_2$)$_{pb+1}$—OH,

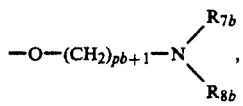

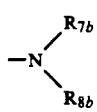

nb represents an integer of 1 to 15) are proposed.

In South African Patent Publication No. 840670, the compounds of the general formula:

$$R_{1c}-S-CH_2-\overset{R_{2c}}{\underset{|}{CH}}-CONH-\overset{R_{3c}}{\underset{|}{CH}}-R_{4c}-COR_{5c} \quad (c)$$

(wherein
R$_{1c}$ represents a hydrogen atom, an acyl group or an aroyl group,
R$_{2c}$ represents a hydrogen atom, an alkyl group, an alkenyl group, an alkynyl group or aralkyl group,
R$_{3c}$ represents a hydrogen atom, an alkyl group, a carboxy group, a carboxyamido group, a substituted alkyl group, a substituted aryl group, a thiol group, an alkylthio group or a heteroaryl group,
R$_{4c}$ represents a group of the formula:

$$\left(\overset{R_{ac}}{\underset{|}{CH}}\right)_{nc},$$

nc represents an integer of 1 to 3,
R$_{5c}$ represents a hydroxy group, an alkoxy group, an aryloxy group, an aralkyloxy group, an NH$_2$ group, or a group of the formula:
NR$_{6c}$R$_{7c}$ or $$HN-\overset{R_{ac}}{\underset{|}{CH}}-COOH)$$

are proposed.
In the U.S. Pat. No. 4,401,677, the compounds of the general formula:

$$HS-CH_2-\overset{R_{1d}}{\underset{|}{CH}}-\overset{O}{\underset{\|}{C}}-NH-\overset{(L)}{\underset{\underset{R_{2d}}{|}}{CH}}-COOH \quad (d)$$

(wherein
R$_{1d}$ represents an alkyl group, a benzyl group or a phenethyl group,
R$_{2d}$ represents an alkyl group or a group of the formula:

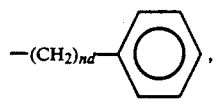

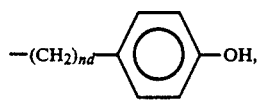

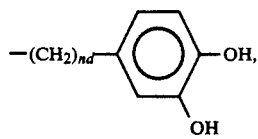

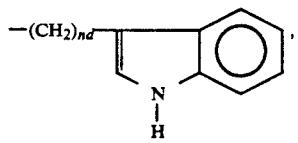

-continued

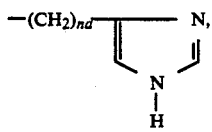

$-(CH_2)_{nd}-NH_2$, $-(CH_2)_{nd}-SH$, $-(CH_2)_{nd}-S-alkyl$,

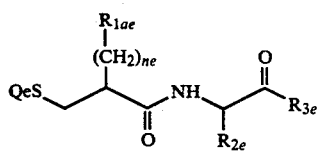

nd represents an integer of 1 to 4) are proposed.

Further, in European Patent Publication No. 254032, the compounds of the general formula:

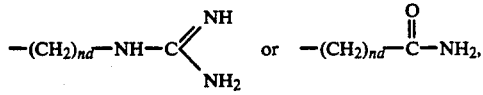

(wherein
$R_{1ae}$ represents a phenyl group substituted by one or more substituents independently selected from alkyl, alkoxy, cycloalkyl etc.

$R_{2e}$ represents a group of the formula: $R_{13e}CONH(CH_2)_{qe^-}$, $R_{13e}NHCO(CH_2)_{qe^-}$, $R_{6e}O-CO(CH_2)_{qe^-}$ etc., $R_{3e}$ represents a group of the formula: $-OR_{7e}$, $-NR_{7e}R_{8e}$ etc., $R_{13e}$ represents a group of the formula: $Y_{1e}-C_6H_4-$ etc., $R_{6e}$, $R_{7e}$ and $R_{8e}$ represent independently a hydrogen atom, an alkyl group, an arylalkyl group etc., ne represents zero or an integer 1 or 2, qe represents an integer 1 to 4, Qe represents a hydrogen atom or a group of the formula: $R_{10e}CO-$, $R_{10e}$ represents an alkyl group, a group of the formula: $Y_{3e}-C_6H_4-$ etc., $Y_{1e}$ and $Y_{3e}$ represent independently a hydrogen atom, an alkyl group, cycloalkyl group, an alkoxy group etc.) are proposed.

OBJECTS

Energetic investigation has been carried out in order to discover compounds having an inhibitory effect on enkephalinase, and the present inventors have found that derivatives wherein (1) a glycine moiety in thiorphan is replaced by an acidic α-amino acid (e.g. aspartic acid, glutamic acid etc.) and further (2) either carboxyl group of the said acidic amino acids is converted into an amido bond with various aromatic amines, have an inhibitory effect on enkephalinase, and have accomplished the present invention.

Accordingly, the present invention relates to the amino acid derivatives of the general formula:

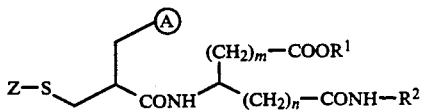

(wherein
$R^1$ represents a hydrogen atom or an alkyl group of 1 to 4 carbon atoms, $R^2$ represents a carbocyclic or heterocyclic ring, unsubstituted or substituted by 1 to 3 $R^3$s, $R^3$ represents independently:
(1) a halogen atom,
(2) a trihalomethyl group,
(3) a hydroxy group,
(4) an alkyl group of 1 to 15 carbon atoms,
(5) an alkoxy group of 1 to 4 carbon atoms,
(6) an alkylthio, alkylsulfinyl or alkylsulfonyl group, of 1 to 4 carbon atoms,
(7) a group of the formula:

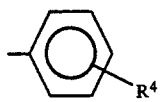

in which $R^4$ represents a hydrogen atom, a halogen atom, a trihalomethyl group, a hydroxy group, an alkyl group of 1 to 4 carbon atoms or an alkoxy group of 1 to 4 carbon atoms (8) a group of the formula:

$-NR^5R^6$ in which $R^5$ and $R^6$ independently represent a hydrogen atom or an alkyl group of 1 to 4 carbon atoms, (9) a group of the formula:

$-CO-R^7$ in which $R^7$ represents an alkyl group of 1 to 4 carbon atoms or a phenyl group substituted by $R^4$ (in which $R^4$ is as hereinbefore defined),

(10) a group of the formula:

$-COOR^8$ in which $R^8$ represents a hydrogen atom or an alkyl group of 1 to 4 carbon atoms,

(11) a group of the formula:

$-CONR^5R^6$ in which $R^5$ and $R^6$ are as hereinbefore defined,

(12) a group of the formula:

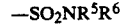

$-SO_2NR^5R^6$ in which $R^5$ and $R^6$ are as hereinbefore defined,

(13) a cyano group,
(14) a nitro group, or
(15) a group of the formula:

$-NHCO-R^7$, in which $R^7$ is as hereinbefore defined,

Z represents:
(1) a hydrogen atom, (2) a group of the formula:

—COR⁹ in which $R^9$ represents an alkyl group of 1 to 4 carbon atoms or a phenyl group substituted by $R^{10}$, in which $R^{10}$ represents a hydrogen atom, a halogen atom, a trihalomethyl group, an alkyl group of 1 to 4 carbon atoms or an alkoxy group of 1 to 4 carbon atoms, (3) a group of the formula:

in which $R^{10}$ is as hereinbefore defined, (4) a group of the formula:

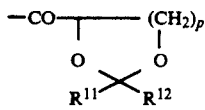

in which $R^{11}$ and $R^{12}$ independently represent a hydrogen atom, an alkyl group of 1 to 4 carbon atoms or a phenyl group substituted by $R^{10}$, in which $R^{10}$ is as hereinbefore defined, or $R^{11}$ and $R^{12}$ together represent an alkylene group of 4 or 5 carbon atoms and p is an integer of 1 or 2, (5) a group of the formula:

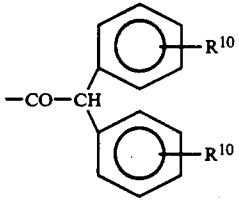

in which two $R^{10}$ are independently as hereinbefore defined, (6) a group of the formula:

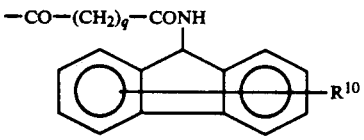

in which $R^{10}$ is as hereinbefore defined and q is an integer of 1 to 4, (7) a group of the formula:

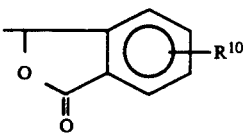

in which $R^{10}$ is as hereinbefore defined, (A) represents a phenyl or cycloalkyl group of 4 to 7 carbon atoms, substituted by $R^{13}$, in which $R^{13}$ represents a hydrogen atom, a halogen atom, a trihalomethyl group, an alkyl group of 1 to 4 carbon atoms or an alkoxy group of 1 to 4 carbon atoms, and m and n represent:
(1) when m is zero, n is an integer of 1 to 4, and
(2) when n is zero, m is an integer of 1 to 4), or non-toxic salts or non-toxic acid addition salts thereof, the process for the preparation of the derivatives of the general formula (I), and enkephalinase inhibitors containing, as active ingredient, the derivatives of the general formula (I) or non-toxic salts thereof.

The derivatives of the general formula (I) can be classified into two groups, i.e. α-amide derivatives of the general formula:

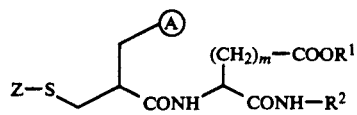

(Ia)

(wherein the various symbols are as hereinbefore defined) and derivatives introduced an amido bond into β-position or after, of the general formula:

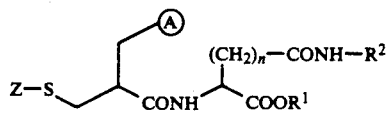

(Ib)

(wherein the various symbols are as hereinbefore defined).

There is no description of the compounds of the general formula (Ia) in any of the prior art including the general formulae (a) to (e) mentioned above, and therefore, the compounds of the general formula (Ia) are novel.

A part of the compounds of the general formula (Ib) are broadly disclosed in European Patent Publication No. 254032 (the general formula (e) hereinbefore described). However, the description in the said European Patent Publication is very broad and in such descriptions, no compounds are disclosed which had introduced an amido bond into the β-position or after nor were any compounds practically prepared. Further the biological activity of the compounds was not confirmed. The present applicants have synthesized many compounds within the general formula (Ib) and confirmed that they have a useful biological activity.

In the general formula (I), the alkyl groups of 1 to 4 carbon atoms, represented by $R^1$, $R^4$, $R^5$, $R^6$, $R^7$, $R^8$, $R^9$, $R^{10}$, $R^{11}$, $R^{12}$ and $R^{13}$ are methyl, ethyl, propyl and butyl groups, and isomers thereof.

The alkoxy groups of 1 to 4 carbon atoms, represented by $R^3$, $R^4$, $R^{10}$ and $R^{13}$ are methoxy, ethoxy, propoxy and butoxy groups, and isomers thereof.

The alkylthio groups of 1 to 4 carbon atoms, represented by $R^3$ are methylthio, ethylthio, propylthio and butylthio groups, and isomers thereof, and the alkylsulfinyl groups of 1 to 4 carbon atoms are methylsulfinyl, ethylsulfinyl, propylsulfinyl and butylsulfinyl groups, and isomers thereof, and further the alkylsulfonyl groups of 1 to 4 carbon atoms are methylsulfonyl, ethylsulfonyl, propylsulfonyl and butylsulfonyl groups, and isomers thereof.

The alkyl groups of 1 to 15 carbon atoms, represented by $R^3$ are methyl, ethyl, propyl, butyl, pentyl, hexyl, heptyl, octyl, nonyl, decyl, undecyl, dodecyl, tridecyl, tetradecyl and pentadecyl groups, and isomers thereof.

The halogen atoms represented by $R^3$, $R^4$, $R^{10}$ and $R^{13}$ are fluorine, chlorine, bromine and iodine atoms, and the trihalomethyl groups represented by $R^3$, $R^4$, $R^{10}$ and $R^{13}$ are trifluoromethyl, trichloromethyl, tribromomethyl and triiodomethyl groups.

The alkylene group of 4 or 5 carbon atoms, represented by $R^{11}$ and $R^{12}$ together, are tetramethylene or pentamethylene group.

In the general formula (I), the carbocyclic rings represented by $R^2$ mean mono-, bi- or tri-cyclic aromatic carbocyclic rings containing not more than 15 carbon atoms, which may be partially or fully saturated.

Examples of the rings mentioned above are benzene, naphthalene, indene, azulene, fluorene, phenanthrene, anthracene, acenaphthalene, biphenylene rings and partially of fully saturated rings thereof.

More preferably, the carbocyclic ring is mono-, bi- or tri-cyclic aromatic ring composed of benzene skeletons, i.e. benzene, naphthalene, phenanthrene and anthracene.

In the general formula (I), the heterocyclic rings represented by $R^2$ mean mono-, bi- or tri-aromatic heterocyclic rings containing not more than 15 carbon and hetero atoms which may be partially or fully saturated.

Examples of the rings mentioned above are furan, thiophene, pyrrole, oxazole, isoxazole, thiazole, isothiazole, imidazole, pyrazole, furazan, pyran, pyridine, pyridazine, pyrimidine, pyrazine, indole, isoindole, benzofuran, benzothiophene, indolizine, benzimidazole, benzthiazole, benzoxazole, chromene, quinoline, isoquinoline, quinolizine, purine, indazole, quinazoline, cinnoline, quinoxaline, phthalazine, pteridine, benzodiazepine carbazole, acridine, phenanthridine, xanthene, phenazine, phenothiazine rings and partially or fully saturated rings thereof.

More preferably, the heterocyclic ring is mono-ring or bi-ring condensed with a benzene ring, containing one or two nitrogen and/or sulfur atoms.

Especially preferred rings represented by R2 are benzene, naphthalene, furan, thiophen, pyridine, pyrimidine, pyrazine, benzimidazole, benzthiazole, benzoxazole and benzodiazepine rings and partially saturated rings thereof.

In the general formula (I), the cycloalkyl groups of 4 to 7 carbon atoms, represented by Ⓐ ring are cyclobutyl, cyclopentyl, cyclohexyl and cycloheptyl groups.

When n is zero, Ⓐ preferably represents a phenyl group or cycloalkyl group of 4 to 7 carbon atoms, each of which is substituted by $R^{13}$ ($R^{13}$ is as hereinbefore defind) and when m is zero, Ⓐ preferably represents an unsubstituted phenyl gorup, or cycloalkyl group of 4 to 7 carbon atoms which is substituted by $R^{13}$ ($R^{13}$ is as hereinbefore defined).

In the general formula (I), the amino acid residue represented by

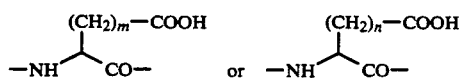

is preferably L-amino acid residue.

The compounds of the general formula (I), of the present invention may be converted into the corresponding salts by known methods. Non-toxic and water-soluble salts are preferable. Suitable salts are salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

The compounds of the general formula (I), if desired, may be converted into acid addition salts by the known methods. Preferably, acid addition salts are non-toxic salts and water-soluble. The suitable acid addition salts are, for example, salts of an inorganic acid such as hydrochloric acid, hydrobromic acid, hydroiodic acid, sulfuric acid, phosphoric acid, nitric acid, or an organic acid such as acetic acid, lactic acid, tartaric acid, benzoic acid, citric acid, methanesulphonic acid, ethanesulphonic acid, benzenesulphonic acid, toluenesulphonic acid, isethionic acid, glucuronic acid and gluconic acid.

The compounds of the general formula (I) can be named as derivatives of an amino acid. For example, the compound of the formula:

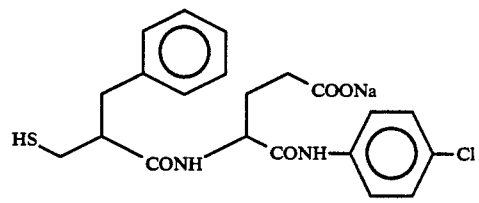

can be called N-(3-mercapto-2-benzylpropionyl)-α-(4-chloroanilino) glutamic acid γ-sodium salt, and the compound of the formula:

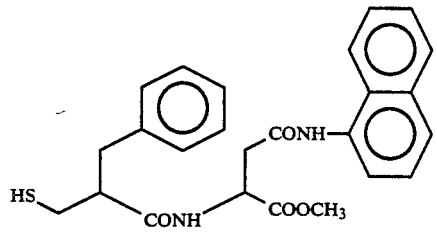

can be called N-(3-mercapto-2-benzylpropionyl)aspartic acid β-(1-naphthyl)amide α-methyl ester.

Throughout the specification including claims, it may be easily understood by those skilled in the art, that the alkyl, alkoxy, alkylthio, alkylsulfinyl and alkylsulfonyl groups include straight-chained and also branched-chained ones.

Accordingly, throughout the specification including claims, all isomers produced by the difference in stereo configuration, such as asymmetric carbons are included in the present invention.

According to the present invention, the compounds of the general formula (I), of the present invention, may be prepared by using a series of reactions depicted in Scheme A, B and C below, wherein $R^{1'}$ represents an alkyl group of 1 to 4 carbon atoms, $R^{14}$ represents a silyl group substituted by three substituents which are selected from an alkyl group of 1 to 4 carbon atoms and a phenyl group (e.g. a tert-butyldimethylsilyl, diphenyl-tert-butylsilyl group), $Z^1$ represents a group of the formula: —$COR^9$ (in whcih $R^9$ is as hereinbefore defined), $Z^2$ represents the group other than a hydrogen atom in the groups represented by Z (Z is as hereinbefore defined), $m_1$ and $n_1$ represent:
(1) when $m_1$ is zero, $n_1$ is an integer of 1 to 4, and
(2) when $n_1$ is zero, $m_1$ is an integer of 2 to 4, $^tBu$ represents a tert-butyl group;
Bn represents a benzyl group, and
the other symbols are as hereinbefore defined.

Scheme A

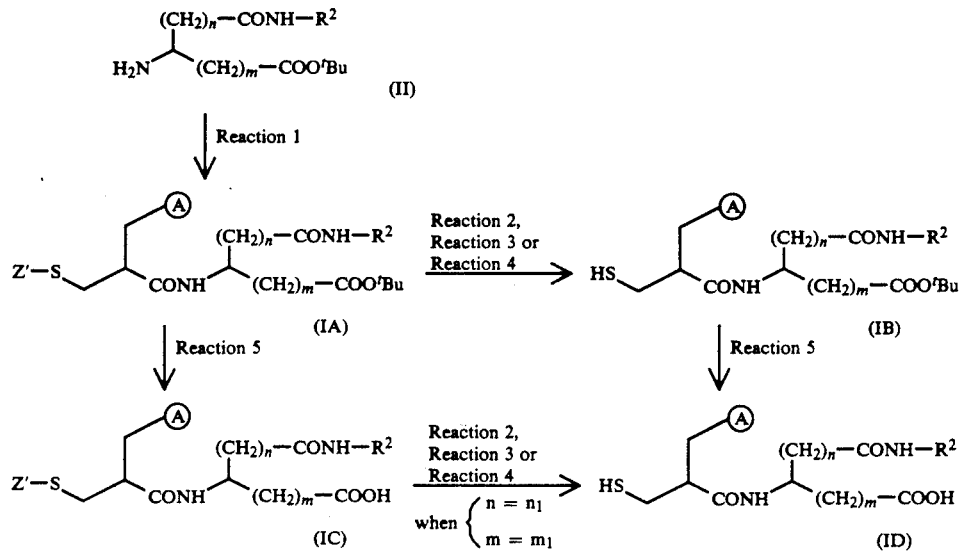

Scheme B

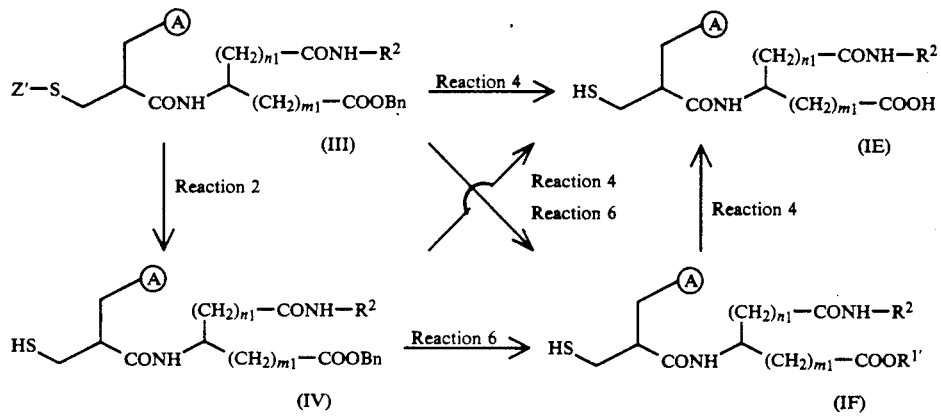

fore defined),

Scheme C

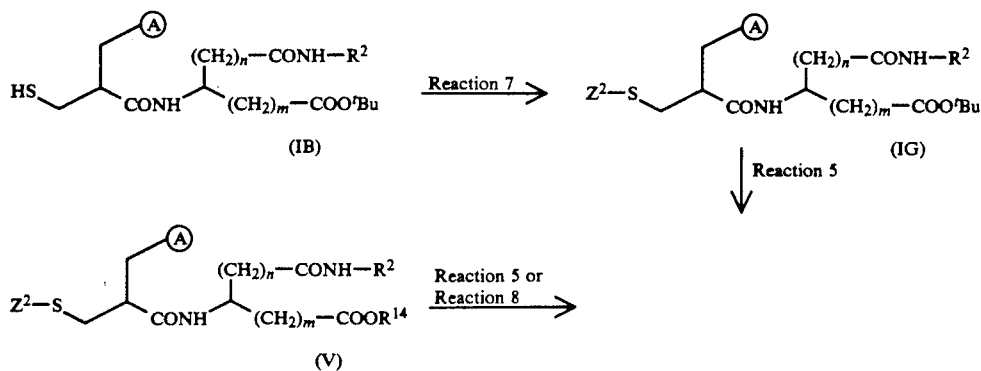

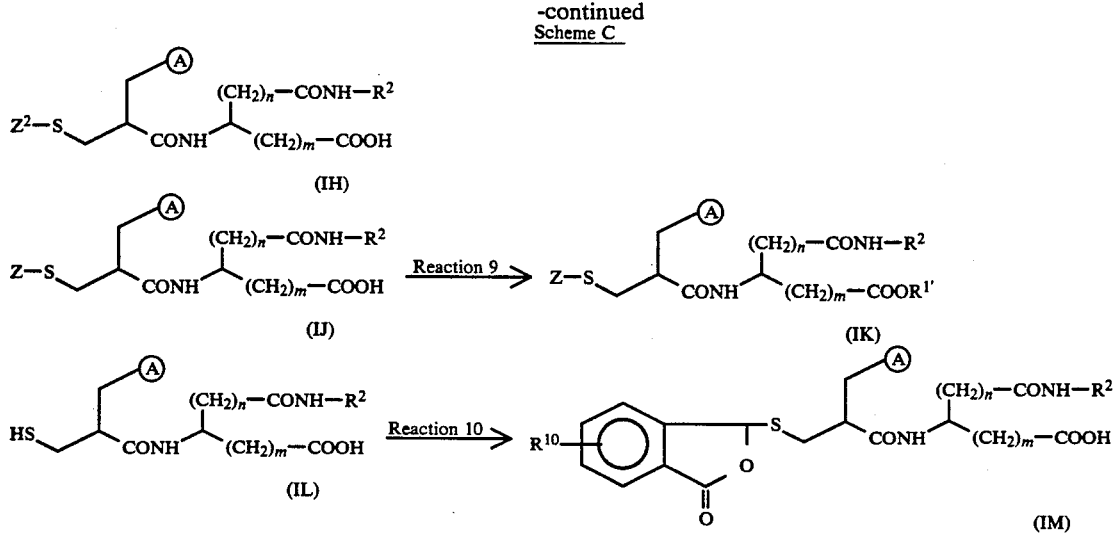

Each of the steps depicted in the said schemes, are well known to those skilled in the art. For example, Reaction 1 may be carried out by reacting an amine of the formula (II) with a carboxylic acid of the formula:

(wherein the various symbols are as hereinbefore defined) to form an amido bond. The said reactions are known and, for example are (A) method using a mixed acid anhydride,
(B) method using an acid halide,
(C) method using a condensing agent such as DCC etc.

DETAILED DESCRIPTION OF THE REACTIONS

The foregoing reactions (A), (B) and (C) are described in greater detailed wherein:

(A) is a method using a mixed acid anhydride which may be carried out, for example, by reacting carboxylic acid of the general formula (VI) and an acid halide (pivaloyl chloride, tosyl chloride, mesyl chloride etc.) or an acid derivative (ethyl chloroformate, isobutyl chloroformate etc.) in the presence of a tertiary amine (pyridine, triethylamine, picoline etc.) in an inert organic solvent (chloroform, methylene chloride, diethyl ether, THF etc.) or without a solvent at a temperature of from 0° C. to 40° C., and then reacting the obtained mixed acid anhydride with an amine of the general formula (II) in an inert organic solvent (as hereinbefore described), at a temperature of from 0° C. to 40° C., (B) is a method using an acid halide which may be carried out, for example, by reacting a carboxylic acid of the general formula (VI) with an acid halide (thionyl chloride, oxalyl chloride etc.) in an inert organic solvent (as hereinbefore describe) or without a solvent at from −20° C. to the reflux temperature of a solvent, and then reacting the obtained acid halide with an amine of the general formula (II) in the presence or absence of a tertiary amine (as hereinbefore described) in an inert organic solvent (as hereinbefore described), at a temperature of from 0° C. to 40° C., and (C) is a method using a condensing agent such as DCC (dicyclohexylcarbodiimide) etc. which may be carried out, for example, by reacting a carboxylic acid of the general formula (VI) with an amine of the general formula (II) using DCC in the presence or absence of a tertiary amine (as hereinbefore described), in an inert organic solvent (as hereinbefore described) or without a solvent, at a temperature of from 0° C. to 40° C.

The reactions of (A), (B) and (C) hereinbefore described are preferably carried out in an atmosphere of inert gas (argon, nitrogen etc.) under anhydrous conditions.

Reaction 2 may be carried out by reacting with 2-mercaptoethylamine ($HS-(CH_2)_2-NH_2$) in an inert organic solvent (methylene chloride, acetonitrile etc.), at a temperature of from ambient to 60° C.

Reaction 3 may be carried out by reacting with anhydrous potassium carbonate or anhydrous sodium carbonate in an absolute alkanol (e.g. absolute methanol, absolute ethanol etc.), ordinarily at a temperature of from −10° C. to 100° C.

Reaction 4 may be carried out by using an aqueous solution of an alkali (potassium hydroxide, sodium hydroxide, lithium hydroxide, potassium carbonate, sodium carbonate etc.) in a water-miscible organic solvent (dimethoxyethane, THF (tetrahydrofuran), dioxane, lower alkanol etc.), ordinarily at a temperature of from −10° C. to 100° C.

Reaction 5 is a hydrolysis under acidic conditions, and may be carried out by reacting with an aqueous solution of an organic acid (acetic acid, oxalic acid, p-toluenesulfonic acid, trifluoroacetic acid etc.) or with an aqueous solution of an inorganic acid (hydrochloric acid, sulfuric acid etc.) in an inert organic solvent (e.g. methylene chloride, THF, dioxane, a lower alkanol etc), at a temperature of from ambient to a reflux temperature of a solvent.

Reaction 6 may be carried out by reacting with anhydrous potassium carbonate or anhydrous sodium carbonate in an absolute alkanol corresponding to the desirable $R^{1a}$ (absolute methanol or absolute ethanol etc.), ordinarily at a temperature of from −10° C. to 100° C.

Reaction 7, when $Z^2$ is a substituted acyl group (the groups of (2)~(6) in those represented by Z), may be carried out by reacting with a halide or acid anhydride of the carboxylic acid corresponding to $Z^2$, in the presence of a tertiary amine (pyridine, triethylamine etc.), in an inert organic solvent (methylene chloride, dimethylformamide, THF, ethyl acetate etc.) or in the absense of a solvent, at a temperature of from 0° C. to 50° C., or when $Z^2$ represents a group of the formula:

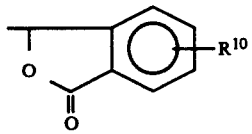

(in which $R^{10}$ is as hereinbefore defined), may be carried out by reacting with a halide of the compound represented by $Z^2$, in the presence of a base (a tertiary amine, a hydroxide or carbonate, of an alkali metal etc.), in an inert organic solvent (methylene chloride, dimethylformamide, THF, acetone etc.) at a temperature of from 10° C. to 50° C.

Reaction 8 is a desilylation, and may be carried out by using tetrabutylammonium fluoride ($_nB_{u4}N^+F^-$) in tetrahydrofuran at room temperature.

Reaction 9 is an esterification, and may be carried out by reacting with a desirable diazoalkane (diazomethane etc.), in an inert organic solvent (diethyl ether, ethyl acetate, methylene chloride, acetone, a lower alkanol etc.) at a temperature of from $-10°$ C. to 40° C., or by reacting a desirable alkanol in the presence of an acid (hydrochloric acid, p-toluenesulfonic acid etc.) or in the presence of a condensing agent (dicyclohexylcarbodiimide etc.), at a temperature of from $-10°$ C. to 50° C.

Reaction 10 may be carried out by the same procedure as Reaction 7 when $Z^2$ represent a group of the formula:

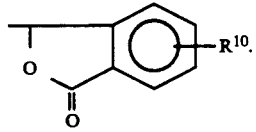

The compounds of the general formulae (II), (III), (IV) and (V), used in the aforesaid schemes, may be prepared by the combination of known methods, for example, by using a series of reactions depicted in the following Scheme D, wherein Boc represents a tert-butoxycarbonyl group, cbz represents a benzyloxycarbonyl group and the other symbols are as hereinbefore defined.

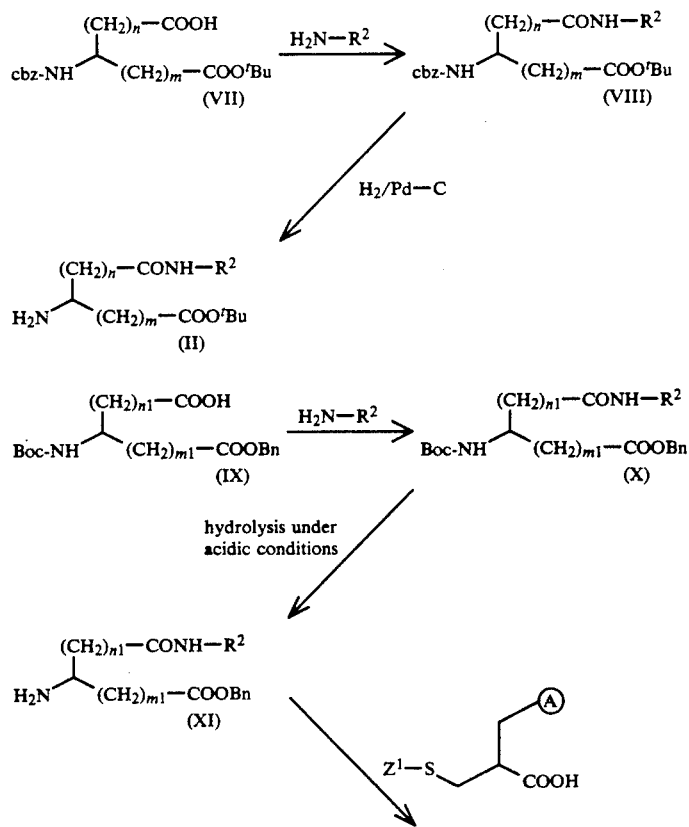

Scheme D

Scheme D -continued

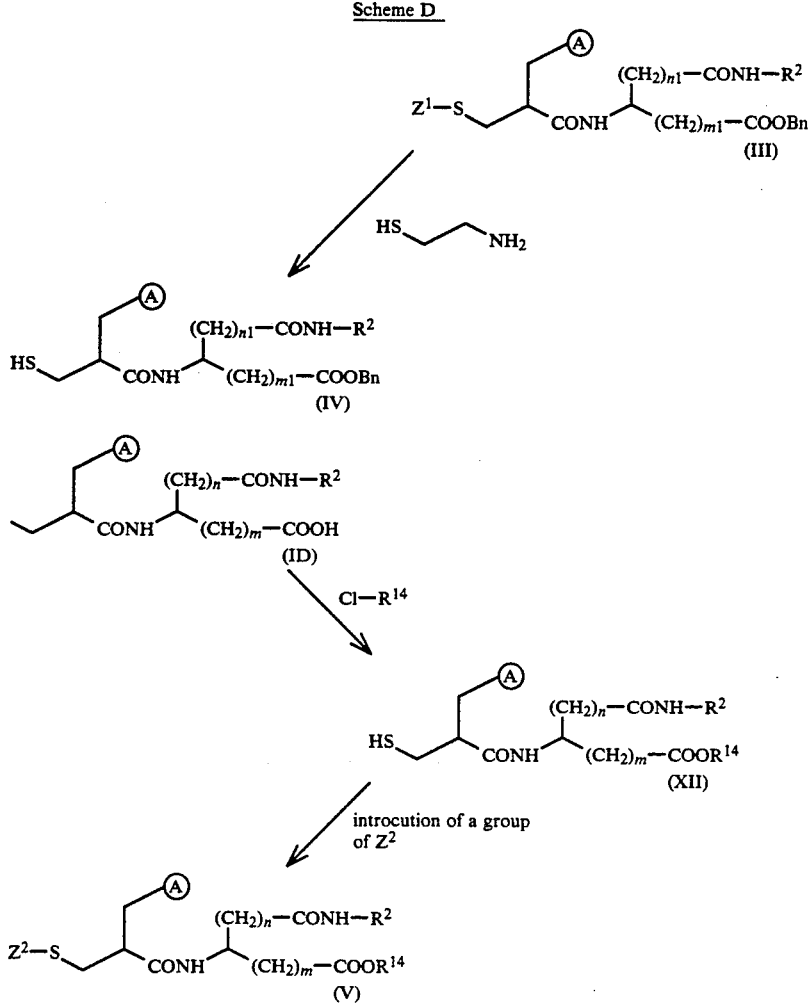

Each of the steps depicted in the said scheme are well known to those skilled in the art.

Throughout the specification, in each reactions, products may be purified by conventional methods, for example, distillation at atmospheric or reduced pressure, high performance liquid chromatography, thin layer chromatography or column chromatography using silica gel or magnesium silicate or washing or recrystallization. Purification may be carried out after each reaction, or after a series of reactions.

Starting materials of the formula (VII) and (IX) and every reagents, used in the process for the preparation, of the present invention, are known compounds per se, or may be easily prepared by known methods.

For example, the compounds of the formula (VII), wherein n is zero and m is 1 or 2, that of the formula (IX), wherein $n_1$ is zero and $m_1$ is 1 or 2, and that of the formula (IX), wherein $m_1$ is zero and $n_1$ is 1 or 2, are on the market.

The compounds of the general formula (I) or non-toxic salts thereof, of the present invention have an inhibitory effect on enkephalinase, and are, therefore, useful as analgesic, antianxiety agents or anticonvulsant, in mammals, especially in humans.

The inhibitory effect on enkephalinase and analgesic effect based on the inhibitory effect, of the compounds of the present invention were confirmed by screening tests as described below.

Inhibitory effect on enkephalinase (1) Method

Enkephalinase was obtained by the procedure as described in Journal of Neurochemistry, 39, 1081 (1982). That is, to striata obtained from ddY male mice (weighing 28~30 g), Tris hydrochloric acid buffer solution (referred to "Tris buffer" hereafter) was added. The mixture was homogenised and centrifuged (1000 g×5 minites). The supernatant obtained was further centrifuged (20000 g×1 minutes). The resulting pellet was washed with cold Tris buffer and resuspended in a fresh Tris buffer to use as enzyme source of enkephalinase.

The experiment was carried out according to the method as described in Journal of Biological Chemistry, 255, 2227 (1980). That is, the test compounds ($10^{-5} \sim 10^{-9}$ M) were dissolved in 2% DMSO/Tris buffer (50 μl). Incubation at 37° C. for 60 minutes was started by adding thereto 150 μg of enzyme solution (×30 dilution of the above enzyme source) and 50 μl of a substrate solution containing succinyl-alanyl-alanyl-phenylalanyl (7-amido-4-methyl)coumarin (i.e. Suc-Ala-Ala-Phe-AMC, final concentration: $10^{-4}$ M) dissolved in 50 mM HEPES/NaOH buffer (pH 7.4). The reaction was stopped by the addition of thiorphan ($10^{-6}$ M) and by heating the samples at 95° C. for 15 minutes. In a second step, the incubation medium was further incubated at 56° C. for 60 minutes in the presence of 0.75 μl of aminopeptidase M. The appearance of AMC fluorescence was measured (exc. 367 nm, em. 440 nm). Blanks values were obtained by the same procedure as above described by using thiorphan ($10^{-6}$ M) instead of the test compound.

(2) Result

The results are shown in Table I below.

TABLE I

Inhibitory effect on enkephalinase (1)

| Compounds Example No. | R¹ | Structure R² | m | Inhibitory effect (IC₅₀, M) |
|---|---|---|---|---|
| 1 | H | phenyl | 2 | $2.1 \times 10^{-8}$ |
| 8(4) | H | -C₆H₄-OCH₃ | 1 | $5.0 \times 10^{-8}$ |
| 3(2) | H | -C₆H₄-COOH | 2 | $3.6 \times 10^{-9}$ |
| 3(8) | H | -C₆H₄-SO₂NH₂ | 2 | $2.3 \times 10^{-8}$ |
| 2(7) | H | naphthyl | 2 | $3.5 \times 10^{-7}$ |
| 3(4) | H | chloropyridyl | 2 | $3.5 \times 10^{-8}$ |
| 3(9) | H | pyrimidinyl | 2 | $1.9 \times 10^{-7}$ |
| 2(10) | H | benzothiazolyl | 2 | $4.4 \times 10^{-8}$ |
| 4 | CH₃ | 1-methyl-5-methyl-2-(phenylimino-methyl)-benzazepine | 1 | $1.5 \times 10^{-7}$ |

Inhibitory effect on enkephalinase (2)

| Compounds Example No. | R¹ | Structure R² | n | Inhibitory effect (IC₅₀, M) |
|---|---|---|---|---|
| 12 | Na | phenyl | 1 | $1.3 \times 10^{-8}$ |
| 11 | Na | phenyl | 2 | $6.8 \times 10^{-8}$ |
| 12(5) | H | -C₆H₄-I | 1 | $2.8 \times 10^{-9}$ |
| 12(7) | H | -C₆H₄-N(CH₃)₂ | 1 | $2.4 \times 10^{-8}$ |
| 12(8) | H | -C₆H₄-CF₃ | 1 | $2.1 \times 10^{-8}$ |

Inhibitory effect on enkephalinase (3)

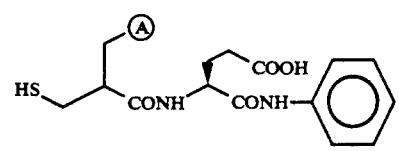

| Compounds Example No. | Structure (A) | Inhibitory effect (IC₅₀, M) |
|---|---|---|
| 1(1) | 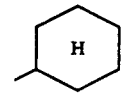 | $4.0 \times 10^{-7}$ |

TABLE I-continued

| | | |
|---|---|---|
| 1(2) | 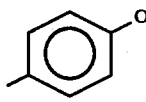 | 5.1 × 10⁻⁸ |
| 1(3) | 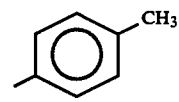 | 7.1 × 10⁻⁸ |

Inhibitory effect on bradykinin-induced biting-like response (1) Method

The experiment was carried out according to the method as described in Journal of Pharmacological Methods, Z, 271 (1982). That is, male Spraque-Dawley rats (weighing 200~300 g) were used. Implantation of the bradykinin (0.63~1.25 μg in 0.5~1.0 μl of distilled water) - filled cannula onto the tooth pulp and the fixation of it on the lower incisor surfaces were carried out under ethyl ether anesthesia. A micro-application of bradykinin onto the tooth pulp produced biting-like response and some other aversive behaviors such as jumping, struggling, rubbing, scratching, escape, head-jerk and body-jerk within 1 minute. Only rats which showed a duration of 20 minutes or more for the biting-like responses before administration of the compound of the present invention, were used for further experiment.

The test compounds suspended in 0.5% carboxymethyl cellulose solution were administered either intraperitoneally or orally. After regular intervals bradykinin was administered. The number of rats which did not show the biting-like response after administration (i.e. analgic state) was counted.

(2) Result

The results are shown in Table II below.

TABLE II

Inhibitory effect on bradykinin-induced biting-like response

| Compounds Example No. | Structure | Dose (mg/kg) | Number of rats | Number of rats which did not show the biting-like response | | | |
|---|---|---|---|---|---|---|---|
| | | | | 10 30 | 40 60 | 70 90 | 100 minutes (i.p.) 120 after (p.o.) |
| 1 | 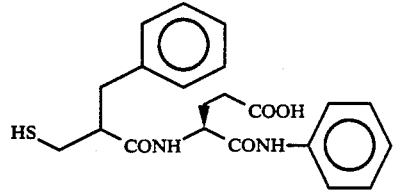 | 10 (i.p.) | 5 | 4 | 4 | 3 | 1 |
| 12(5) | 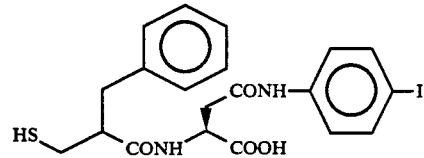 | 10 (i.p.) | 8 | 4 | 2 | 1 | 0 |
| 16 | 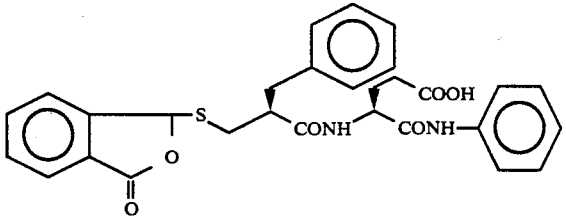 | 100 (p.o.) | 8 | 3 | 6 | 2 | 0 |
| 13(5) | 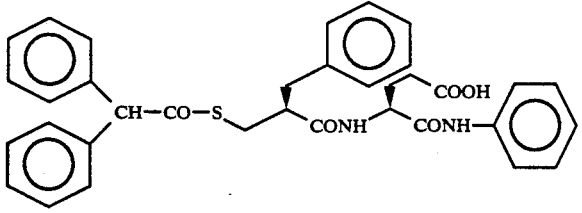 | 100 (p.o.) | 8 | 1 | 7 | 1 | 1 |

On the other hand, it was confirmed that the acute toxicity of the compound of the present invention were very weak. For example, acute toxiety (LD$_{50}$) of N-[3-(phthalid-3-yl)thio-2S-benzylpropionyl]-α-anilino-L-glutamic acid is 500-1000 mg/kg in intraperitoneal injection in mice. Therefore, the compounds of the present invention may be considered to be sufficiently safe and suitable for pharmaceutical used.

For the purpose above described, the compounds of the present invention may normally be administered systemically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 10 mg and 1 g, by oral administration, up to several times, preferably 1 to 4 times, per day, and between 1 mg and 100 mg, by parenteral administration (preferably, intravenous administration) up to several times, preferably 1 to 4 times, per day.

As mentioned above, the doses to be used depend upon various conditions. Therefore, there are cases in which doses lower than or greater than the ranges specified above may be used.

The compounds of the present invention were administered as solid compositions, liquid compositions and other compositions for oral administration and injections, external compositions and suppositories etc. For parenteral administration.

Solid compositions for oral administration, included compressed tablets, pills, capsules, dispersible powders, and granules. In such compositions, one or more of the active compounds are admixed with at least one inert diluent (lactose, mannitol, glucose, hydroxypropylcellulose, microcrystalline cellulose, starch, polyvinylpyrrolidone, magnesium metasilicate aluminate etc.).

The compositions may also comprise, as is normal practice, additional substances other than inert diluents, e.g. lubricating agents (magnesium stearate etc.), disintegrating agents (cellulose calcium glycolate etc.), and assisting agent for dissolving (glutamic acid, aspertic acid etc.) and stabilizing agent (lactose etc.).

The tablets or pills may, if desired, be coated with film of gastric or enteric material (sugar, gelatin, hydroxypropylcellulose, hydroxypropylmetnyl cellulose phthalate etc.).

The term "capsules" include both soft and hard ones.

Liquid compositions of oral administration include pharmaceutically-acceptable solutions, emulsions, suspensions, syrups and elixirs.

In such liquid compositions, one or more of the active compounds are admixed with inert diluents commonly used in the art (purified water, ethanol etc.).

Besides inert diluents, such compositions may also comprise adjuvants such as wetting agents and suspending agents, sweetening agents, flavouring agents, perfuming agents and preserving agents.

Other compositions for oral administration include spray compositions which may be prepared by know methods and which comprise one or more of the active compounds. Spray compositions may comprise additional substances other than inert diluents, e.g. stabilizing agents (sodium sulfite etc.), isotonic buffer (sodium chloride, sodium citrate, citric acid etc.). For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions.

In such injections, one or more of active compounds are admixed with at least one of inert aqueous diluents (distilled water for injection, physiological salt solution etc.) or inert non-aqueous diluents (propylene glycol, polyethylene glycol, olive oil, ethanol, POLYSOLBATE 80 (registered trade mark) etc.).

Injections may comprise the addition of other than inert diluents, e.g. preserving agents, wetting agents, emulsifying agents, dispersing agents, stabilizing agents (lactose etc.), assisting agents such as assisting agents for dissolving (glutamic acid, aspertic acid etc.).

They may be usually sterilized by filtration (through a bacteria-retaining filter etc.), incorporation of sterilizing agents in the compositions or by irradiation. After sterilizing as described, they also be manufactured in the form of sterile solid compositions, for example, by freeze-drying, and which can be dissolved in sterile water or some other sterile diluents for injection immediately before used.

Other compositions for parenteral administration include liquids for external use, and endermic liniments (ointment etc.), suppositories and pessaries which comprise one or more of the active compounds and may be prepared by known methods.

The following reference examples and examples illustrate, but not limit, the present invention.

The solvents in the parentheses show the eluting or developing solvents and the ratios of the solvents used are by volume in chromatographic separations. Unless otherwise specified, "IR" was measured by KBr method and "NMR" was measured in deuterochloroform (CDCl₃) solution.

REFERENCE EXAMPLE 1

N-(tert-butoxycarbonyl)-α-anilino-L-glutamic acid γ-benzyl ester

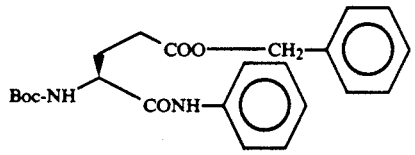

To a solution of N-(tert-butoxycarbonyl)-L-glutamic acid γ-benzyl ester dicyclohexylamine salt (being on a market, 5.18 g) in methylene chloride (30 ml) was added pivaloyl chloride (1.35 ml) under cooling with ice, and the mixture was stirred for 10 minutes at room temperature. The reaction mixture was again cooled with ice, and then a solution of aniline (1 ml) in triethylamine (1.4 ml) was added dropwise thereto, and the mixture was stirred for 20 minutes at room temperature. The reaction mixture was diluted with ethyl acetate, washed with 1N hydrochloric acid, 1N aqueous solution of sodium hydroxide and a stirred aqueous solution of sodium chloride, successively, dried over magnesium sulfate, and concentrated under reduced pressure.

The residue (solid) was washed with n-hexane to give the title compound (2.9 g) having the following physical data:

TLC (ethyl acetate:n-hexane=1:1):Rf 0.74;

NMR: δ 8.40 (1 H, brs), 7.55~6.90 (10 H, m), 5.35 (1 H, brd), 5.10 (2 H, s), 4.40~4.10 (1 H, m), 2.80~2.40 (2 H, m), 2.40~1.70 (2 H, m), 1.42 (9 H, s);

MS:m/z 412(M+), 356, 339, 292.

REFERENCE EXAMPLE 2

α-anilino-L-glutamic acid γ-benzyl ester trifluoroacetic acid salt

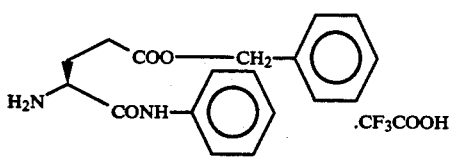

To a solution of glutamic acid protected by a Boc group (2.9 g prepared in Reference Example 1) in methylene chloride (2 ml) was added trifluoroacetic acid (5.4 ml) under cooling with ice, and the mixture was stirred for 2.5 hours at a room temperature. The reaction mixture was concentrated under reduced pressure to give the crude title compound (3.00 g) having the following physical data:

TLC (ethyl acetate):Rf 0.23;
NMR: δ 9.50(1 H, brs), 7.60~6.80(10 H, m), 5.00(2 H, s), 4.60~4.30(1 H, m), 2.70~2.50(2 H, m), 2.50~1.90(2 H, m);
MS:m/z 312, 204, 193, 192.

REFERENCE EXAMPLE 3

N-(3-acethylthio-2RS-benzylpropionyl)-α-anilino-L-glutamic acid γ-benzyl ester

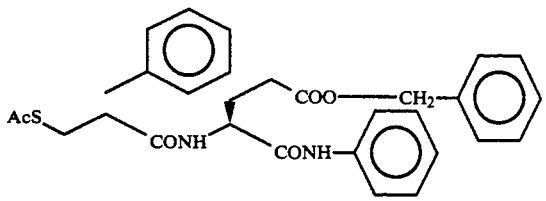

To a solution of 3-acethylthio-2RS-benzylpropionic acid (prepared by the methods described hereafter, 833 mg) in methylene chloride (1 ml) was added an excess amount of oxalyl chloride at room temperature, and the mixture was stirred for 30 minutes. Oxalyl chloride was fully distilled off from the reaction mixture, and to the residue was added methylene chloride (2 ml) to obtain a solution of acid chloride.

To a solution of trifluoroacetic acid salt of the amine compound (prepared in Reference Example 2, 1.64 g) in a mixture of pyridine (2.83 ml) and methylene chloride (16 ml), was added dropwise the solution of acid chloride prepared hereinbefore under cooling with ice and the mixture was stirred for 15 minutes at room temperature. The reaction mixture was poured into water, washed with 1N hydrochloric acid, 1N aqueous solution of sodium hydroxide and a saturated aqueous solution of sodium chloride, successively, dried over magnesium sulfate and concentrated under reduced pressure.

The residue was purified by column chromatography on silica gel (methylene chloride-n:hexane =2:1→methylene chloride →methylene chloride:methanol=20:1) and further recyrstallized from a mixture of ethyl acetate and n-hexane to give the title compound (743 mg) as white powder having the following physical data:

TLC (ethyl acetate:n-hexane=1:1):Rf 0.48;
NMR: δ 8.52 and 8.38(1 H, brs), 7.34~7.00(15 H, m), 6.44~6.24(1 H, m), 5.12 and 5.10(2 H, s), 4.60~4.30(1 H, m), 3.24~3.00 and 3.00~2.82(4 H, m), 2.76~2.34(3 H, m), 2.28 and 2.22(3 H, m), 2.20~1.82(2 H, m);
MS:m/z 532(M+) 489, 440, 370.

3-Acetylthio-2RS-benzylpropionic acid, used as a starting material in a procedure hereinbefore described, was prepared as follows.

To 2RS-benzylacrylic acid (being on the market, 25 g) was added thioacetic acid (16 ml) and the mixture was refluxed for one hour by heating on oil bath. An excess amount of thioacetic acid was distilled off from the residue and further distilled off as azeotropic mixture with toluene. The reside was purified by column chromatography on silica gel (ethyl acetate:n-hexane:acetic acid=5:95:0.05→20:80:0.05) to give 3-acetylthio-2RS-benzylpropionic acid (16.7 g) as colorless oil having the following physical data:

TLC (n-hexane:ethyl acetate=1:1):Rf 0.3;
NMR: δ 7.35~7.14(5 H, m), 3.2~2.8(5 H, m), 2.33(3 H, s);
Ms:m/z 238(M+), 220.

EXAMPLE 1

N-(3-mercapto-2RS-benzylpropionyl)-α-anilino-L-glutamic acid and their γ-sodium salt

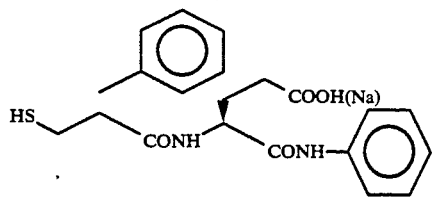

Under an atmosphere of argon, to a solution of the benzyl ester compound (prepared in Reference Example 3, 743 mg) in a mixture of tetrahydrofuran (9 ml) and dimethoxyethane (1.4 ml) was added a solution of lithium hydroxide monohydrate (293 mg) in water (5 ml) at room temperature and the mixture was stirred for 30 minutes at the same temperature. To the reaction mixture was added 1N hydrochloride acid under cooling with ice to acidify and the mixture was extracted with ethyl acetate. The extract was washed with a saturated aqueous solution of sodium chloride, dried over sodium sulfate and concentrated under reduced pressure.

The residue was purified by column chromatography on silica gel (chloroform→acetic acid:-chloroform=1:99) to give the title compound (387 mg as free acid) as white powder having the following physical data:

Melting point: 158.5°~160.0° C.;
TLC (acetic acid:chloroform=5:95): Rf 0.20;
NMR(CDCl3+DMSO-d6): δ 9.04~8.86(1 H, d like m)), 7.56~7.40(2 H, m), 7.36~6.92(9 H, m), 4.72~4.46(1 H, m), 3.02~2.40(6 H, m), 2.40~1.68(4 H, m), 1.54(1 H, t);
MS:m/z 400(M+), 382, 366, 353, 335;
IR(KBr): ν 3275, 1700, 1640, 1600, 1540, 1440, 1300, 1250, 750, 695 cm−1.

The free acid compound obtained was dissolved in a small amount of methanol and 1N aqueous solution of sodium hydroxide and water were added thereto and the mixture was stirred for 5 minutes at room temperature. The reaction was lyophilized to give the title compound (as sodium salt) having the following physical data:

using a corresponding 3-acetylthio-2-substituted propionic acid.

TABLE III

Structure: HS-CH2-CH(CH2-A)-CONH-CH(CH2COOH)-CONH-phenyl

| Example No. | (A) | Chemical name | TLC | IR (ν, cm$^{-1}$) |
|---|---|---|---|---|
| 1(1) | cyclohexyl-H | N-(3-mercapto-2RS-cyclohexylmethyl-propionyl)-α-anilino-L-glutamic acid | Rf 0.33 (acetic acid: chloroform = 5:95) | 3600~2400, 1710, 1640, 1540, 1440, 1245, 755 |
| 1(2) | 4-OCH$_3$-phenyl | N-[3-mercapto-2RS-(4-methoxybenzyl)-propionyl]-α-anilino-L-glutamic acid | Rf 0.40 (acetic acid: chloroform = 1:9) | 3650~2250, (3270, 3040, 2920), 1700~1600(1630), 1505, 1440, 1295, 1240, 1175, 1115, 750, 690 |
| 1(3) | 4-CH$_3$-phenyl | N-[3-mercapto-2RS-(4-methylbenzyl)-propionyl]-α-anilino-L-glutamic acid | Rf 0.47 (acetic acid: chloroform = 1:9) | 3650~2200(3270, 3040, 2925), 1705, 1640, 1600, 1540, 1440, 1305, 1250, 755 |

TLC (chloroform:acetic acid=95:5): Rf 0.20;
NMR(CD$_3$OD): δ 7.60~7.00(10 H, m), 4.50~4.20(1 H, m), 3.05~1.70(9 H, m);
IR: ν 3680~2500(3270) 1635, 1595, 1540, 1440, 1400, 1310, 1250, 750, 695 cm$^{-1}$.

The desired compounds shown in the following Table III were obtained by the same procedure as a series of reactions of Reference Example 1→Reference Example 2→Reference Example 3→Example 1, by

EXAMPLE 2

The desired compounds shown in the following Table IV were obtained by the same procedure as a series of reactions of Reference Example 1→Reference Example 2 (hydrochloric acid instead of trifluoroacetic acid was used)→Reference Example 3→Example 1, by using corresponding starting material and the amine compound.

TABLE IV

Structure: HS-CH2-CH(CH2-phenyl)-CONH-CH(CH2COOH)-CONH-R$^2$

| Example No. | R$^2$ | Chemical name | TLC | IR (ν, cm$^{-1}$) or Melting point |
|---|---|---|---|---|
| 2(1) | 4-F-phenyl | N-(3-mercapto-2RS-benzylpropionyl)-α-(4-fluoroanilino)-L-glutamic acid | Rf 0.19 (acetic acid: chloroform = 8:92) | 3275, 1705, 1640, 1540, 1505, 1440, 1405 |
| 2(2) | 4-Cl-phenyl | N-(3-mercapto-2RS-benzylpropionyl)-α-(4-chloroanilino)-L-glutamic acid | Rf 0.28 (acetic acid: chloroform = 8:92) | 3275, 1705, 1640, 1600, 1530, 1495 |
| 2(3) | 4-I-phenyl | N-(3-mercapto-2RS-benzylpropionyl)-α-(4-iodoanilino)-L-glutamic acid | Rf 0.34 (acetic acid: chloroform = 8:92) | 181.0~185.0° C. |
| 2(4) | 4-OCH$_3$-phenyl | N-(3-mercapto-2RS-benzylpropionyl)-α-(4-methoxyanilino)-L-glutamic acid | Rf 0.25 (acetic acid: chloroform = 2:8) | 3275, 1700, 1640, 1510, 1440, 1420, 1300, 1240 |

TABLE IV-continued

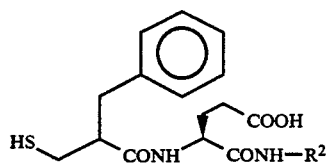

| Example No. | R² | Chemical name | TLC | IR ($\nu$, cm$^{-1}$) or Melting point |
|---|---|---|---|---|
| 2(5) | —⟨⟩—CF₃ | N-(3-mercapto-2RS-benzylpropionyl)-α-(4-trifluoromethylanilino)-L-glutamic acid | Rf 0.28 (acetic acid: chloroform = 5:95) | 3275, 1700, 1690, 1640, 1610, 1520, 1410 |
| 2(6) | —⟨⟩—N(CH₃)₂ | N-(3-mercapto-2RS-benzylpropionyl)-α-[4-(N,N-dimethylamino)anilino]-L-glutamic acid | Rf 0.43 (chloroform:methanol: acetic acid = 30:3:1) | 3275, 1710, 1650, 1640, 1520, 1450 |
| 2(7) | (1-naphthyl) | N-(3-mercapto-2RS-benzylpropionyl)-L-glutamic acid α-(1-naphthyl)amide | Rf 0.25 (acetic acid: chloroform = 5:95) | 3625~2300(3260, 3025), 1695, 1630, 1525, 1500, 1430, 1395, 1265, 790, 770, 695 |
| 2(8) | —⟨⟩—CH₃ | N-(3-mercapto-2RS-benzylpropionyl)-α-(4-methylanilino)-L-glutamic acid | Rf 0.29 (acetic acid: chloroform = 8:92) | 3275, 1710, 1660, 1640, 1610, 1540, 1530, 1510, 1440, 1410 |
| 2(9) | —⟨N⟩ | N-(3-mercapto-2RS-benzylpropionyl)-L-glutamic acid α-(4-pyridyl)amide | Rf 0.18 (chloroform:methanol: acetic acid = 30:5:1) | 3250, 1720, 1700, 1630, 1590, 1500 |
| 2(10) | 2-benzthiazolyl | N-(3-mercapto-2RS-benzylpropionyl)-L-glutamic acid α-(2-benzthiazolyl)amide | Rf 0.52 (chloroform:methanol: acetic acid = 30:3:1) | 3650~2150(3275, 3050, 2925), 1700, 1640, 1530, 1440, 1305, 1285, 750, 700 |

EXAMPLE 3

The desired compounds shown in the following Table V and VI were obtained by the same procedure as a series of reactions of Reference Example 1 (the amido bond-forming reaction using dicyclohexylcarbodiimide (DDC) as a condensing agent, was used instead of the method using a mixed acid anhydride with pivaloyl chloride)→Reference Example 2 (hydrochloride acid instead of trifluoroacetic acid was sued)→Reference Example 3→Example 1, by using a corresponding starting material and the amine compound.

TABLE V

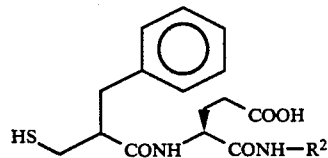

| Example No. | R² | Chemical name | TLC | IR ($\nu$, cm$^{-1}$) |
|---|---|---|---|---|
| 3(1) | —⟨⟩—CN | N-(3-mercapto-2RS-benzylpropionyl)-α-(4-cyanoanilino)-L-glutamic acid | Rf 0.36 (acetic acid: chloroform = 1:9) | 3650~2320(3300), 2240, 1690, 1640, 1590, 1410, 1310, 1255, 1180, 840, 755, 700, 555 |

TABLE V-continued

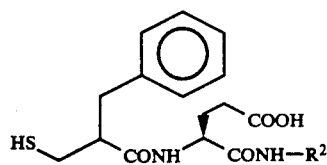

| Example No. | R² | Chemical name | TLC | IR (ν, cm⁻¹) |
|---|---|---|---|---|
| 3(2) | —⟨phenyl⟩—COOH | N-(3-mercapto-2RS-benzylpropionyl)-α-(4-carboxyanilino)-L-glutamic acid | Rf 0.39 (chloroform:methanol: acetic acid = 30:3:1) | 3700~2340(3270, 3050), 1690, 1680, 1640, 1595, 1525, 1410, 1250, 1175, 1005, 855, 775, 700 |
| 3(3) | —⟨phenyl⟩—COCH₃ | N-(3-mercapto-2RS-benzylpropionyl)-α-(4-acetylanilino)-L-glutamic acid | Rf 0.34 (acetic acid: chloroform = 1:9) | 3670~2330(3350), 1710, 1640, 1595, 1525, 1405, 1360, 1320, 1270, 1180, 840, 700 |
| 3(4) | —⟨5-chloropyridin-2-yl⟩ | N-(3-mercapto-2RS-benzylpropionyl)-L-glutamic acid α-(5-chloropyridin-2-yl)amide | Rf 0.41 (acetic acid: chloroform = 5:95) | 3640~2200(3300, 3050), 1705, 1640, 1580, 1520, 1460, 1380, 1305, 1115, 700 |
| 3(5) | —⟨phenyl⟩—NO₂ | N-(3-mercapto-2RS-benzylpropionyl)-α-(4-nitroanilino)-L-glutamic acid | Rf 0.17 (acetic acid: chloroform = 4:96) | 3300, 1710, 1645, 1620, 1600, 1500, 1450, 1415, 1340 |
| 3(6) | —⟨phenyl⟩—CONH₂ | N-(3-mercapto-2RS-benzylpropionyl)-α-(4-carbamoylanilino)-L-glutamic acid | Rf 0.38 (acetic acid: ethyl acetate = 5:95) | 3300, 1710 (shoulder), 1700~1660 (shoulder), 1640, 1605, 1520, 1410 |
| 3(7) | —⟨phenyl⟩—(CH₂)₉CH₃ | N-(3-mercapto-2RS-benzylpropionyl)-α-(4-decylanilino)-L-glutamic acid | Rf 0.46 (acetic acid: chloroform = 5:95) | 3280, 2940, 2860, 1700, 1680, 1600, 1515, 1445, 1410 1255, 700 |
| 3(8) | —⟨phenyl⟩—SO₂NH₂ | N-(3-mercapto-2RS-benzylpropionyl)-α-(4-sulfamoylanilino)-L-glutamic acid | Rf 0.52 (acetic acid: ethyl acetate = 5:95) | 3300, 1700 (shoulder), 1645, 1595, 1520, 1400, 1330, 1255, 1160 |
| 3(9) | —⟨pyrazin-2-yl⟩ | N-(3-mercapto-2RS-benzylpropionyl)-L-glutamic acid α-(pyrazin-2-yl)amide | Rf 0.26 (acetic acid: chloroform = 1:9) | 3650~2240(3275, 3040, 2930), 1705, 1630, 1530, 1410, 1300, 1270, 1210, 1060, 1010, 845, 750, 700 |
| 3(10) | —⟨pyrimidin-2-yl⟩ | N-(3-mercapto-2RS-benzylpropionyl)-L-glutamic acid α-(pyrimidin-2-yl)amide | Rf 0.26 (chloroform:methanol: acetic acid = 30;3:1) | 3250, 1710, 1650, 1580, 1510, 1440, 1415 |
| 3(11) | —⟨2-iodophenyl⟩ | N-(3-mercapto-2RS-benzylpropionyl)-α-(2-iodoanilino)-L-glutamic acid | Rf 0.24 (acetic acid: chloroform = 5:95) | 3250, 3025, 1700, 1630, 1575, 1515, 1430, 1280, 1010, 750, 700 |
| 3(12) | —⟨3-iodophenyl⟩ | N-(3-mercapto-2RS-benzylpropionyl)-α-(3-iodoanilino)-L-glutamic acid | Rf 0.24 (acetic acid: chloroform = 5:95) | 3260, 3030, 1705, 1635, 1580, 1520, 1470, 1410, 1300, 1240, 865, 780, 750, 700, 680 |

TABLE VI

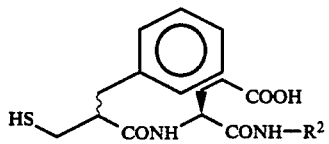

| Example No. | R² | Chemical name | TLC | Optical rotation ([α]_D) |
|---|---|---|---|---|
| 3(13) | ![N-benzthiazolyl] (∿= ◀) | N-(3-mercapto-2S-benzylpropionyl)-L-glutamic acid α-(2-benzthiazolyl) amide | Rf 0.25 (acetic acid: chloroform = 5:95) | +9.83° (CHCl₃, c = 1.005) |
| 3(14) | ![N-benzthiazolyl] (∿= ·····) | N-(3-mercapto-2R-benzylpropionyl)-L-glutamic acid α-(2-benzthiazolyl) amide | Rf 0.29 (chloroform:tetrahydrofuran: acetic acid = 30:8:1) | −35.6° (CHCl₃, c = 1.00) |

EXAMPLE 4

N-(3-mercapto-2RS-benzylpropionyl)-L-aspartic acid α-(2,3-dihydro-1-methyl-5-phenyl-1H-1,4-benzodiazepin-7yl)amide β-methyl ester

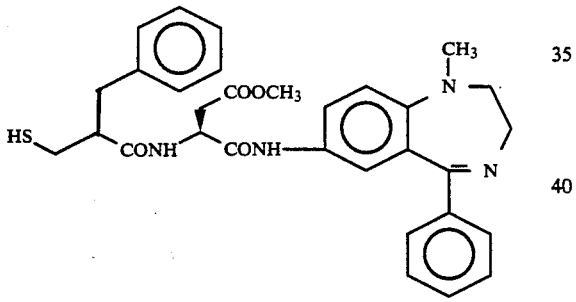

To a solution of N-(3-acetylthio-2RS-benzylpropionyl)-L-aspartic acid α-(2,3-dihydro-1-methyl-5-phenyl-1H-1,4-benzodiazepin-7-yl) amide β-benzyl ester (prepared by the same procedure as a series of reactions of Reference Example 1→Reference Example 2=Reference Example 3, by using the corresponding starting materials, 1,686 g) in methanol (10 ml) was added potassium carbonate (0.688 g), and the mixture was stirred for one hour at room temperature. The reaction mixture was diluted with methylene chloride (100 ml), washed with water and a saturated aqueous solution of sodium chloride, dried over magnesium sulfate and concentrated under reduced pressure. The residue was purified by column chromatography on silica gel (methylene chloride : methanol=30 : 1) to give the title compound (0.735 g) as orange amorphous solid having the following physical data:

TLC (methylene chloride : methanol=95 : 5) : Rf 0.37;

NMR: δ8.32 and 7.98(1H, s), 7.68∼6.64(14H, m), 4.90∼4.75(1H, m), 3.88∼3.40(7H, m), 3.20∼1.92(10H, m), 1.40(1H, 2xt);

MS:m/z 558(M+), 526, 510, 498:

IR(kBr): ν3600∼2500, 1715, 1650, 1610, 1490, 1290, 1180, 690.

The following desired compound was obtained by the same procedure as above.

(1) N-(3-mercapto-2RS-benzylpropionyl)-L-glutamic acid α-(2,3-dihydro-1-methyl-5-phenyl-1H-1,4-benzodiazepin-7-yl)amide γ-methyl ester

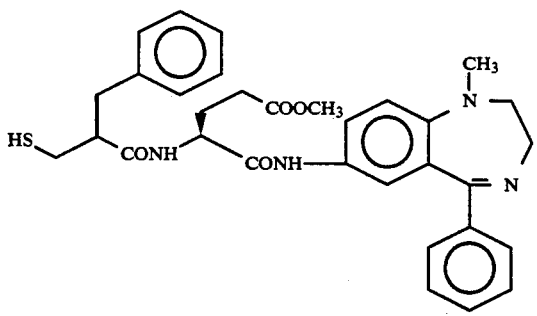

TLC (methanol : methylene chloride=1 : 9) : Rf 0.56;

NMR: δ8.48 and 8.27 (1H, s, 5 : 6), 7.70∼6.90(13H, m), 6.70 and 6.52(1H, d), 4.55∼4.28 (1H, m), 3.80∼3.50(4H, m), 3,63 and 3.65(3H, s), 3.00∼1.84(9H, m), 2.80 and 2.76(3H, s), 1.44 and 1.39(1H, t);

MS:m/z 572(M+), 540, 512;

IR: ν3300, 1740, 1650, 1500.

EXAMPLE 5

N-(3-mercapto-2RS-benzylpropionyl)-L-glutamic acid α-(2,3-dihydro-1-methyl-5phenyl-1H-1,4-benzodiazepin-7yl)amide

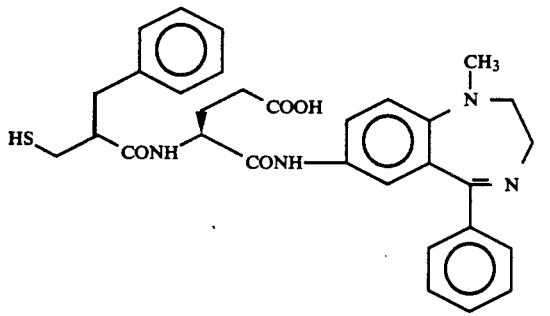

The title compound having the following physical data was obtained by the same procedure as Example 1, by using the methyl ester prepared in Example 4(1).

TLC (methanol : benzene=2 : 8) : Rf 0.2;
Melting point : 126.0°~131.0° C.

REFERENCE EXAMPLE 4

α-anilino-L-glutamic acid γ-tert-butyl ester

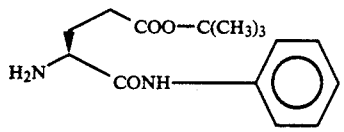

Under an atmosphere of hydrogen, a mixture of N-(benzyloxycarbonyl)-α-anilino-L-glutamic acid γ-tert-butyl ester (7.80 g, prepared by the same procedure as Reference Example 1 (the amido bond forming reaction using DCC as a condensing agent, was used instead of the method using a mixed acid anhydride) by using N-(benzyloxycarbonyl)-L-glutamic acid γ-tert-butyl ester as starting material), palladium-carbon (10% ; 880 mg) and ethyl acetate (130 ml) was stirred for 3 hours at a room temperature. The reaction mixture was filtered, and to the filtrate was added ethyl acetate (20 ml) containing 4N hydrogen chloride, and then the mixture was concentrated under reduced pressure to give hydrochloric acid salt of the title compound as crude product.

EXAMPLE 6

N-(3-benzoylthio-2S-benzylpropionyl)-α-anilino-L-glutamic acid γ-tert-butyl ester

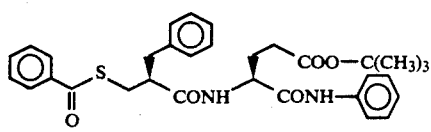

The title compound having the following physical data was obtained by the same procedure as Reference Example 3, by using the amine compound prepared in Reference Example 4 and 3-benzoylthio-2S-benzylpropionic acid.

TLC (n-hexane : ethyl acetate=1 : 1) : Rf 0.56.

EXAMPLE 7

N-(3-mercapto-2S-benzylpropionyl)-α-anilino-L-glutamic acid γ-tert-butyl ester

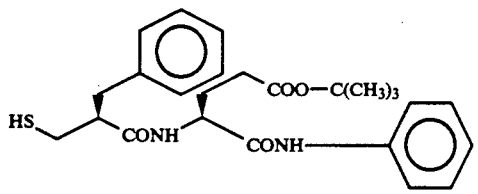

The title compound having the following physical data was obtained by the same procedure as Example 4, by using the benzoyl compound prepared in Example 6.

TLC (n-hexane : ethyl acetate=1 : 1) : Rf 0.53.

EXAMPLE 8

N-(3-mercapto-2S-benzylpropionyl)-α-anilino-L-glutamic acid

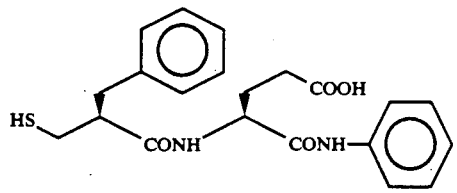

To a solution of the tert-butyl ester (770 mg) prepared in Example 7, in ethyl acetate (3 ml) was added ethyl acetate (2 ml) containing 4N hydrogen chloride, and the mixture was stirred for two hours at a room temperature. The reaction mixture was concentrated under reduced pressure and the residue was purified by column chromatography on silica gel (methylene chloride : ethyl acetate=9 : 1 →4 : 1→2 : 1→ethyl acetate) to give the title compound (300 mg) having the following physical data:

TLC (chloroform : tetrahydrofuran : acetic acid=15 : 4 : 1) : Rf 0.39;

Optical rotation (c=0.895, absolute $C_4H_5OH$) : $[\alpha]_D$−22.2°.

The desired compounds shown in the following Table VII were obtained by the same procedure as a series of reaction of Reference Example 4→Example 6→Example 7→Example 8, by using corresponding starting materials.

TABLE VII

| Example No. | Structure | Chemical name | TLC | Optical rotation ($[\alpha]_D$) or IR ($\nu$, cm$^{-1}$) |
|---|---|---|---|---|
| 8(1) | (structure) | N-(3-mercapto-2R-benzylpropionyl)-α-anilino-L-glutamic acid | Rf 0.30 (acetic acid: chloroform = 5:95) | $[\alpha]_D$ −91.72° (c = 1.01, absolute C$_2$H$_5$OH) |
| 8(2) | (structure) | N-(3-mercapto-2S-benzylpropionyl)-α-anilino-L-aspartic acid | Rf 0.425 (chloroform: tetrahydrofuran: acetic acid = 15:4:1) | $[\alpha]_D$ −28.64° (c = 1.00, CH$_2$OH)) |
| 8(3) | (structure) | N-(3-mercapto-2R-benzylpropionyl)-α-anilino-L-aspartic acid | Rf 0.46 (acetic acid: chloroform = 5:95) (twice developing) | $[\alpha]_D$ − 86.0° (c = 0.82, CH$_3$OH) |
| 8(4) | (structure) | N-(3-mercapto-2RS-benzylpropionyl)-α-(4-methoxyanilino)-L-aspartic acid (less polar isomer) | Rf 0.44 (chloroform: tetrahydrofuran: acetic acid = 15:4:1) | 3290, 3050, 2930, 1705, 1645, 1515, 1410, 1250, 1170, 1030, 825, 700 |

EXAMPLE 9

N-(3-acetylthio-2RS-benzylpropionyl)-γ-anilino-L-glutamic acid α-tert-butyl ester

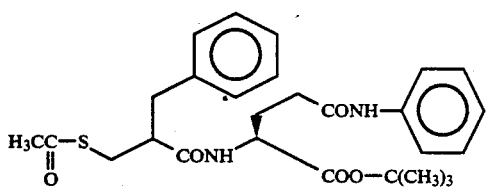

The title compound having the following physical data was obtained by the same procedure as a series of reactions of Reference Example 1→Reference Example 4→Reference Example 3, by using N-(benzyloxycarbonyl)-L-glutamic acid α-tert-butyl ester as starting material.

TLC (ethyl acetate : n-hexane=1 : 1) : Rf 0.42.

EXAMPLE 10

N-(3-acetylthio-2RS-benzylpropionyl)-γ-anilino-L-glutamic acid

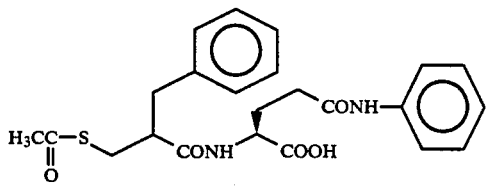

The title compound having the following physical data was obtained by the same procedure as Reference Example 2, by using the tert-butyl ester prepared in Example 9 as starting material.

TLC (ethyl acetate : methanol=9 : 1) : Rf 0.12.

EXAMPLE 11

N-(3-mercapto-2RS-benzylpropionyl)-γ-anilino-L-glutamic acid α-sodium salt

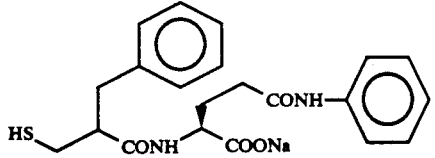

To the acetyl compound (150 mg, prepared in Example 10) in a mixture of chloroform (1 ml) and acetonitrile (2 ml) was added cysteamine (i.e. $H_2N-(CH_2)_2-SH$, 52.2 mg), and the mixture was stirred for 20 minutes at 40° C. The reaction mixture was diluted with ethyl acetate, washed with water, dried over magnesium sulfate and concentrated under reduced pressure. The residue was purified by column chromatography on silica gel (ethyl acetate : n-hexane = 1 : 1) to give the free acid corresponding to the title compound.

The obtained free acid compound was dissolved in a small amount of methanol and 1N aqueous solution of sodium hydroxide and water were added thereto. The mixture was stirred for 5 minutes at room temperature. The reaction mixture was lyophilized to give the title compound (sodium salt) having the following physical data:

Melting point : 131.0°~135° C.;
TLC (chloroform : tetrahydrofuran : acetic acid = 80 : 15 : 5) : Rf 0.23.

EXAMPLE 12

N-(3-mercapto-2RS-benzylpropionyl)-β-anilino-L-aspartic acid and the corresponding α-sodium salt

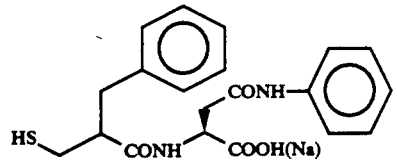

The title compound having the following physical data was obtained by the same procedure as a series of reactions of Reference Example 1→Reference Example 2→Reference Example 3→Example 11, by using N-(tert-butoxycarbonyl)-L-aspartic acid α-benzyl ester as starting material.

(1) free acid

TLC (chloroform : tetrahydrofuran : acetic acid = 15 : 4 : 1) : Rf 0.26 ;
IR: ν3600~2300, 1725, 1650, 1600, 1530, 1440, 755, 695 cm$^{-1}$.

(2) sodium salt

TLC (methylene chloride: tetrahydrofuran : acetic acid = 15 : 4 : 1) : Rf 0.35;
IR: ν3640~2400, 1650, 1630, 1595, 1530, 1390, 1380 cm$^{-1}$.

The desired compounds shown in the following Table VIII were obtained by the same procedure as Example 12 by using corresponding starting materials.

TABLE VIII

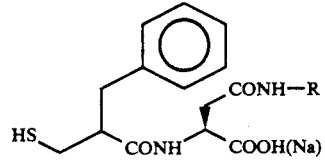

| Example No. | R | Chemical name | TLC | Optical rotation ($[\alpha]_D$) or IR ($\nu$, cm$^{-1}$) |
|---|---|---|---|---|
| 12(1) | phenyl (Na salt) | N-(3-mercapto-2RS-benzylpropionyl)-β-anilino-L-aspartic acid α-sodium salt (more polar isomer) | Rf 0.31 (chloroform: tetrahydrofuran: acetic acid = 15:4:1) | $[\alpha]_D$ +22.2° (c = 1.53, absolute $C_2H_5OH$) (as free acid) |
| 12(2) | phenyl (Na salt) | N-(3-mercapto-2RS-benzylpropionyl)-β-anilino-L-aspartic acid α-sodium salt (less polar isomer) | Rf 0.30 (chloroform: tetrahydrofuran: acetic acid = 15:4:1) | $[\alpha]_D$ −6.73° (c = 1.54, absolute $C_2H_5OH$) (as free acid) |
| 12(3) | 4-F-phenyl | N-(3-mercapto-2RS-benzylpropionyl)-β-(4-fluoroanilino)-L-aspartic acid | Rf 0.36 (chloroform: methanol: acetic acid = 30:5:1) | 3650~2200(3280), 1715, 1650, 1525, 1500, 1405, 1210, 825 |
| 12(4) | 4-Cl-phenyl | N-(3-mercapto-2RS-benzylpropionyl)-β-(4-chloroanilino)-L-aspartic acid | Rf 0.38 (chloroform: methanol: acetic acid = 30:5:1) | 3645~2200(3290), 1715, 1655, 1600, 1530, 1490, 1400 |

TABLE VIII-continued

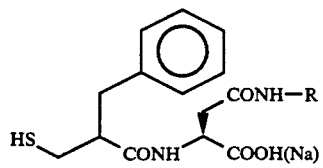

| Example No. | R | Chemical name | TLC | Optical rotation ($[\alpha]_D$) or IR ($\nu$, cm$^{-1}$) |
|---|---|---|---|---|
| 12(5) | —⟨phenyl⟩—I | N-(3-mercapto-2RS-benzylpropionyl)-β-(4-iodoanilino)-L-aspartic acid | Rf 0.40 (chloroform: methanol: acetic acid = 30:5:1) | 3650~2200(3280), 1720, 1650, 1590, 1515, 1480, 1400, 810 |
| 12(6) | —⟨phenyl⟩—OCH$_3$ | N-(3-mercapto-2RS-benzylpropionyl)-β-(4-methoxyanilino)-L-aspartic acid | Rf 0.38 (chloroform: methanol: acetic acid = 30:3:1) | 3650~2700, 1640, 1600, 1505, 1410, 1245, 1025, 825 |
| 12(7) | —⟨phenyl⟩—N(CH$_3$)$_2$ | N-(3-mercapto-2RS-benzylpropionyl)-β-[4-(N,N-dimethylamino)anilino]-L-aspartic acid | Rf 0.23 (chloroform: methanol: acetic acid = 30:3:1) | 3650~2200(3280), 1650, 1600, 1510, 1310, 820, 700 |
| 12(8) | —⟨phenyl⟩—CF$_3$ | N-(3-mercapto-2RS-benzylpropionyl)-β-(4-trifluoromethylanilino)-L-aspartic acid | Rf 0.33 (chloroform: methanol: acetic acid = 30:3:1) | 3670~2250(3280, 3050, 2920), 1720, 1650, 1605, 1525, 1405, 1320, 1155, 1110, 1065, 840 |
| 12(9) | (2,3-dihydro-1-methyl-5-phenyl-1H-1,4-benzodiazepin-7-yl) | N-(3-mercapto-2RS-benzylpropionyl)-L-aspartic acid β-(2,3-dihydro-1-methyl-5-phenyl-1H-1,4-benzodiazepin-7-yl)amide | Rf 0.15 (methylene chloride: methanol: acetic acid = 16:3:1) | 3650~2400, 1640, 1610, 1520, 1490, 1395, 1295 |

REFERENCE EXAMPLE 5

N-(3-mercapto-2RS-benzylpropionyl)-α-anilino-L-glutamic acid γ-tert-butyl-diphenylsilyl ester

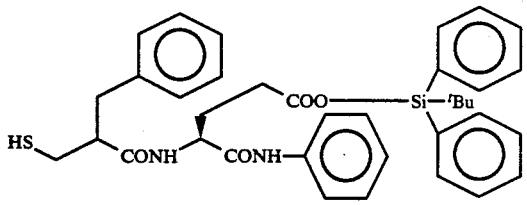

To a solution of the carboxylic acid (1.69 g, prepared in Example 1) in dimethylformamide (12 ml) were added imidazole (0.631 g) and successively tert-butyldiphenylsilyl chloride (1.23 ml) at a room temperature, and the mixture was stirred for 3 hours at the same temperature. The reaction mixture was dissolved in ether (150 ml), washed with 1N hydrochloric acid, 1N aqueous solution of sodium hydroxide and water, successivly, dried over magnesium sulfate and concentrated under reduced pressure. The residue was purified by column chromatography on silica gel (ethyl acetate: methylene chloride=5 : 95→1 : 9) to give the title compound (2.37 g) as white powder having the following physical data:

TLC (ethyl acetate : methylene chloride : 1 : 9) : Rf 0.48;

NMR: δ8.58 and 8.46(1H,x×2), 7.85~6.98(20H, m), 6.84~6.62(1H, d×2), 4.56~4.39(1H, m), 2.98~1.02(19H, m);

MS:m/z 638(M+), 581.

REFERENCE EXAMPLE 6

N-(3-nicotinoylthio-2RS-benzylpropionyl)-α-anilino-L-glutamic acid γ-tert-butyl-diphenylsilyl ester

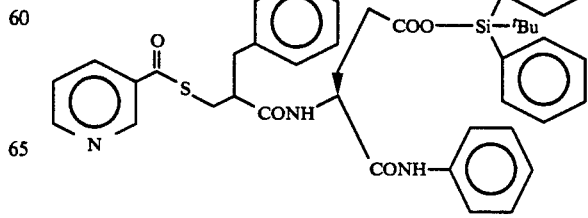

To a mixture of the mercapto compound (1.43 g, prepared in Reference Example 5), nicotinic acid (0.276 g) and diphenylphosphoryl azide (0.99 ml) and dimethylformamide (5 ml), was added triethylamine (0.63 ml) at 0° C. and the mixture was stirred for 3 hours at a room temperature. To the reaction mixture was added water (30 ml) and the mixture was extracted with ethyl acetate (80 ml×2). The extract was dried over magnesium sulfate and concentrated under reduced pressure. The residue was purified by column chromatography on silica gel (methylene chloride : ethyl acetate=3 : 1→2 : 1) to give the title compound (0.35 g) as white powder having the following physical data:

TLC (methylene chloride : ethyl acetate=2 : 1) : Rf 0.44 and 0.38;

NMR: δ9.12 and 9.02(1H, dd×2), 8.73 and 8.70 (1H, dd×2), 8.53 and 8.45(1H, s×2), 8.13 and 7.95(1H, dd×2), 7.75~7.00(21H, m), 6.60~6.42(1H, d×2), 4.52~4.37(1H, m), 3.45~1.50(9H, m), 1.11~1.08(9H, s×2);

MS:m/z 685,547.

REFERENCE EXAMPLE 13

N-(3-nicotinoylthio-2RS-benzylpropionyl)-α-anilino-L-glutamic acid

A solution of the ester compound (350 mg, prepared in Reference Example 6) in a mixture of acetic acid (3 ml), tetrahydrofuran (1 ml) and water (1 ml) was stirred for 16 hours at a room temperature, and the reaction mixture was concentrated under reduced pressure. The residue was purified by column chromatography on silica gel (chloroform : methanol : acetic acid=80 : 3 : 1→50 : 3 : 1) to give the title compound (175 mg) as white powder having the following physical data:

TLC (chloroform : methanol : acetic acid=50 : 3 : 1) : Rf 0.47;

NMR(CDCl$_1$+DMSO—d$_6$): δ9.68 and 9.62(1H, s×2), 9.05 and 9.00 (1H, d×2), 8.77 and 8.73(1H, dd×2), 8.34~8.04(2H, m), 7.60~6.96(11H, m), 4.62~4.36(1H, m), 3.80~1.60(9H, m);

MS:m/z 487, 348, 335;

IR(KBr): ν3600~2100 (3370, 3040, 2925), 1705, 1640, 1635, 1590, 1525, 1440, 1210, 915, 690 cm$^{-1}$.

The desired compounds shown in the following Table IX and X were obtained by the same procedure as a series of reactions of Reference Example 5→Reference Example 6→Example 13, by using corresponding starting materials.

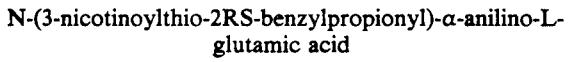

TABLE IX

| Example No. | Structure | Chemical name | TLC | Optical rotation ([α]$_D$) or IR (ν, cm$^{-1}$) |
|---|---|---|---|---|
| 13(1) | 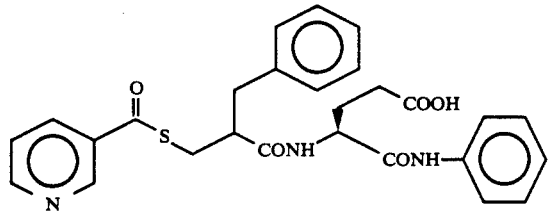 | N-(3-nicotinoylthio-2RS-benzylpropionyl)-β-anilino-L-aspartic acid | Rf 0.37 (chloroform methanol: acetic acid = 30:5:1) | 3650~2200(3275, 3030), 1715, 1660, 1595, 1530, 1435, 1200, 910, 755, 690 |
| 13(2) | 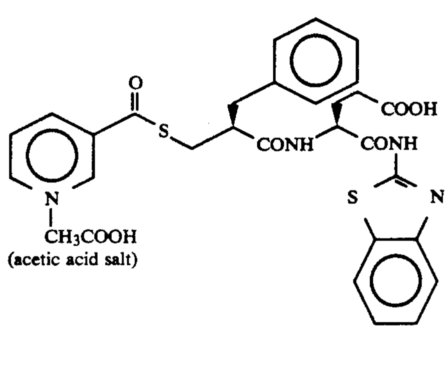 | N-(3-nicotinoylthio-2S-benzylpropionyl)-L-glutamic acid α-(2-benzthiazolyl)amide.acetic acid salt | Rf 0.17 (acetic acid: chloroform = 5:95) | [α]$_D$ −38.6° (c = 0.975, tetrahydrofuran) |

TABLE IX-continued

| Example No. | Structure | Chemical name | TLC | Optical rotation ($[\alpha]_D$) or IR ($\nu$, cm$^{-1}$) |
|---|---|---|---|---|
| 13(3) | (structure shown: 3-nicotinoylthio compound, hydrochloric acid salt) | N-(3-nicotinoylthio-2R-benzylpropionyl)-α-anilino-L-glutamic acid.hydrochloric acid salt | Rf 0.53 (methylene chloride: tetrahydrofuran: acetic acid = 7:2:1) | 3270, 1705 (shoulder), 1665, 1598, 1530, 1442, 1214, 930, 760, 702 |

TABLE X

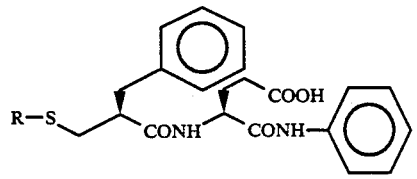

| Example No. | R | Chemical name | TLC | Optical rotation |
|---|---|---|---|---|
| 13(4) | 3-pyridyl-C(=O)– (HCl salt) (hydrochoric acid salt) | N-(3-nicotinoylthio-2S-benzylpropionyl)-α-anilino-L-glutamic acid.hydrochloric acid salt | Rf 0.32 (acetic acid: chloroform = 10:90) | $[\alpha]_D$ −58.6° (c = 1.055, CH$_3$OH) |
| 13(5) | (C$_6$H$_5$)$_2$CH–C(=O)– | N-(3-diphenylacetylthio-2S-benzylpropionyl)-α-anilino-L-glutamic acid | Rf 0.40 (methanol: chloroform = 10:90) | $[\alpha]_D$ −52.9° (c = 1.035, CHCl$_3$) |
| 13(6) | 4-pyridyl-C(=O)– | N-(3-isonicotinoylthio-2S-benzylpropionyl)-α-anilino-L-glutamic acid | Rf 0.36 (chloroform: tetrahydrofuran: acetic acid = 15:4:1) | $[\alpha]_D$ −77.48° (c = 1.00, CH$_3$OH) |
| 13(7) | 2,2-dimethyl-1,3-dioxolan-4S-carbonyl-CH$_2$CH$_2$–C(=O)– | N-[3-(2,2-dimethyl-1,3-dioxolan-4S-carbonyl)thio-2S-benzylpropionyl]-α-anilino-L-glutamic acid | Rf 0.25 (ethyl acetate) | $[\alpha]_D$ −58.80° (c = 1.085, CHCl$_3$) |

TABLE X-continued

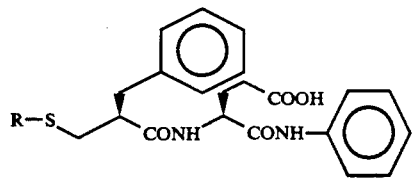

| Example No. | R | Chemical name | TLC | Optical rotation |
|---|---|---|---|---|
| 13(8) | 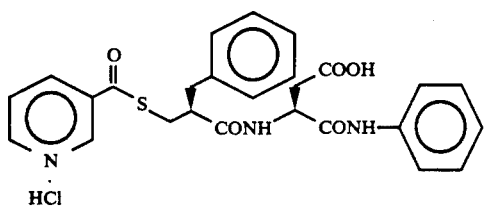 | N-[3-[N-(9-fluorenyl)succinamoyl]thio-2S-benzylpropionyl]-α-anilino-L-glutamic acid | Rf 0.42 (actic acid: chloroform: = 2:98) | [α]$_D$ −127.5° (c = 1.00, dimethyl sulfoxide) |

EXAMPLE 14

N-(3-nicotinoylthio-2S-benzylpropionyl)-α-anilino-L-aspartic acid hydrochloride

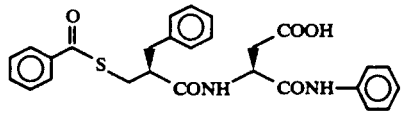

The title compound having the following physical data was obtained by the same procedure as a series of reactions of Reference Example 1 (the amido bond forming reaction using DCC as a condensing agent, was used instead of the method using a mixed acid anhydride)→Reference Example 4→Example 6→Example 7→Reference Example 6→Example 8, by using N-(benzyloxycarbonyl)-L-aspartic acid β-tert-butyl ester dicyclohexylamine salt as starting material.

TLC (methylene chloride : tetrahydrofuran : acetic acid=7 : 2 : 1) : Rf 0.56 ;

Optical rotation (c=1.00, CH$_3$OH) : [a]$_D$−66.22°.

EXAMLE 15

N-(3-benzoylthio-2S-benzylpropionyl)-α-anilino-L-aspartic acid

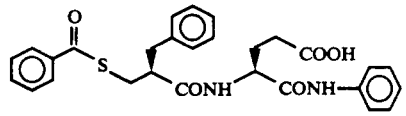

The title compound having the following physical data was obtained by the same procedure as a series of reactions of Reference Example 1 (the amido bond forming reaction using DCC as a condensing agent, was used instead of the method using a mixed acid anhydride)→Reference Example 4→Example 6→Example 10, by using N-(benzyloxycarbonyl)-L-aspartic acid β-tert-butyl ester dicyclohexylamine salt as starting material.

TLC (chloroform : acetic acid=95 : 5) : Rf 0.31;
IR : ν3290, 3040, 1700, 1645, 1600, 1520, 1440, 1200, 1170, 910, 755, 690 cm$^{-1}$.

The following desired compound was obtained by the same procedure as above.

(1)

N-(3-benzoylthio-2S-benzylpropionyl)-α-anilino-L-glutamic acid

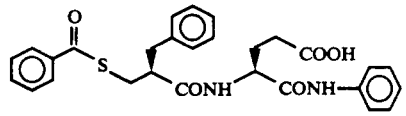

TLC (chloroform : acetic acid=95 : 5) : Rf 0.29;
IR : ν3270, 3050, 1705, 1655, 1640, 1600, 1530, 1490, 1445, 1205, 910, 750, 685 cm$^{-1}$.

REFERENCE EXAMPLE 7

N-[3-(phthalid-3-yl)thio-2S-benzylpropionyl]-α-anilino-L-glutamic acid γ-tert-butyldiphenylsilyl ester

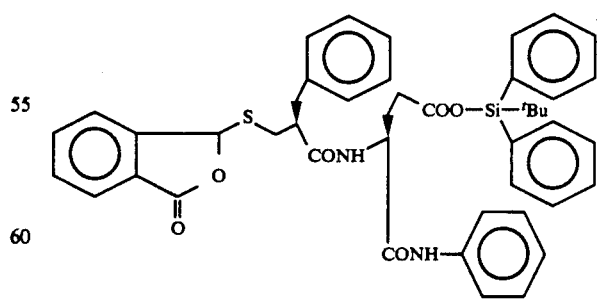

To a solution of the thioether compound (178 mg, prepared by the same procedure as Reference Example 5 by using the compound prepared in Example 8 as starting material) in acetone (2 ml) were added 3-phthalidyl chloride (56.1 mg) and potassium carbonate (46 mg) at room temperature, and the mixture was stirred for 2 hours at the same temperature. The reaction mixture was diluted with a mixture of ethyl acetate and ether, washed with water and a saturated aqueous solution of sodium chloride, successively, dried over sodium sulfate and concentrated under reduced pressure. The residue was purified by column chromatography on silica gel (ethyl acetate: n-hexane = 1 : 2) to give the title compound (153.6 mg) having the following physical data :

TLC (ethyl acetate : n-hexane = 1 : 2) : Rf 0.2

EXAMPLE 16

N-[3-(phthalid-3yl)thio-2S-benzylpropionyl]-α-anilino-L-glutamic acid

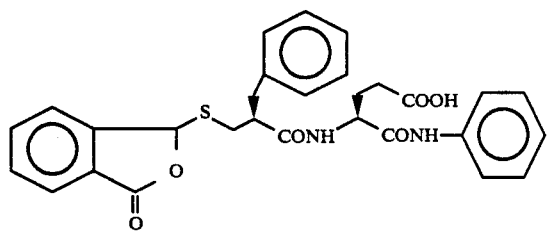

The title compound having the following physical data was obtained by the same procedure as Example 13, by using the silyl ester prepared in Reference Example 7 as starting material.

TLC (chloroform : acetic acid = 95 : 5) : Rf 0.40;
IR : ν3255, 1750, 1640, 1600, 1520, 1440 cm⁻¹.

The following desired compounds were obtained by the same procedure as above.

(1)
N-[3-(phthalid-3yl)thio-2S-benzylpropionyl]-α-anilino-L-aspartic acid

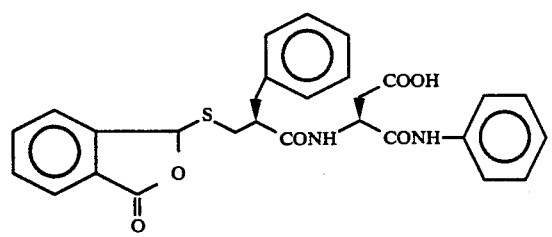

TLC (chloroform : tetrahydrofuran : acetic acid = 15 : 4 : 1) : Rf 0.51;
IR ; ν3280, 3030, 1760, 1640, 1600, 1525, 1440, 1285, 1170, 940, 760, 725, 695 cm⁻¹.

(2)
N-[3-(phthalid-3yl)thio-2S-benzylpropionyl]-L-glutamic acid α-(2-benzthiazolyl)amide

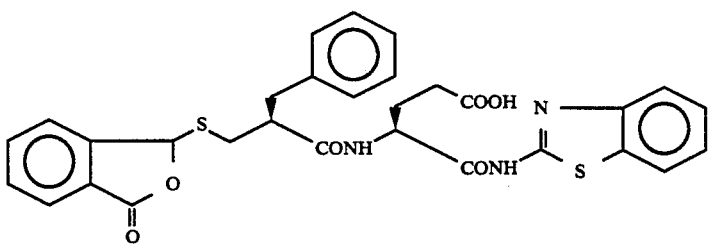

TLC (chloroform : acetic acid = 98 : 2) : Rf 0.25;
IR : ν3300, 1760, 1640, 1600, 1540, 1440 cm⁻¹.

EXAMPLE 17

N-[3-(phthalid-3R(or-3S)-yl)thio-2S-benzylpropionyl]-α-anilino-L-glutamic acid

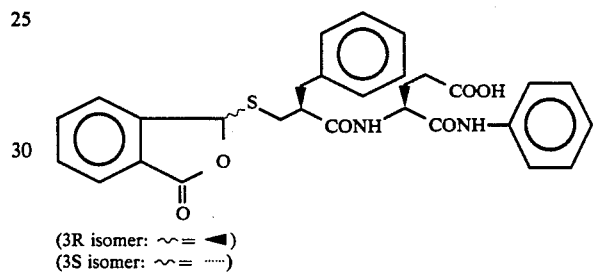

(3R isomer: ∿ = ◀)
(3S isomer: ∿ = ·····)

The diastereomer (i.e. 3RS-mixture, prepared in Example 16) was recrystallized twice from ethyl acetate to give the 3R-isomer having the following physical data. Further, mother liquor obtained in the separation of R-isomer, was concentrated under reduced pressure and the residue was dissolved in ethanol and recrystallized twice from ethanol to give the 3S-isomer having the following physical data.

(1) 3R-isomer

TLC (methylene chloride : methanol = 9 : 1) : Rf 0.14;
IR : ν3270, 3060, 1758, 1732, 1671, 1646, 1531, 1446, 1295, 1177, 960, 756, 697 cm⁻¹.

(2) 3S-isomer

Melting point: 174° ~ 176° C.;
TLC (methylene chloride : methanol = 9 : 1) : Rf 0.12;
IR : ν3286, 3060, 1774, 1709, 1677, 1639, 1533, 1445, 1290, 953, 726, 701 cm⁻¹.

FORMULATION EXAMPLE

The following components were admixed in conventional method and punched out to obtain 100 tablets each containing 50 mg of active ingredient.

| | |
|---|---|
| N-(3-mercapto-2RS-benzylpropionyl)-α-anilino-L-glutamic acid | 5.0 g |
| Cellulose calcium glycolate (disinintegrating agent) | 0.2 g |
| Magnesium stearate (lubricating agent) | 0.1 g |
| Microcrystaline cellulose | 4.7 g |

What is claimed is:
1. An amino acid compound of the formula:

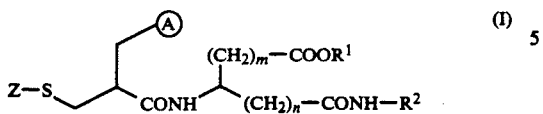 (I)

wherein
R$^1$ represents a hydrogen atom or an alkyl group of 1 to 4 carbon atoms,
R$^2$ represents mono-, bi- or tri-carbocyclic ring(s) containng not more than 15 carbon atoms which may be partially or fully saturated or aromatic or R$^2$ represents heterocyclie ring selected from the group consisting of furan, thiophene, pyrrole, oxazole, isoxazole, thiazole, isothiazole, imidazole, pyrazole, furazan, pyran, pyridine, pyridazine, pyrimidine, pyrazine, indole, isoindole, benzofuran, benzothiophene, indolizine, benzimidazole, benzthiazole, benzoxazole, chromene, quinoline, isoquinoline, quinolizine, purine, indazole, quinazoline, cinnoline, quinoxaline, phthalazine, pteridine, benzodiazepine, carbazole, acridine, phenanthridine, xanthene, phenazine and phenothiazine rings which may be may be partially or fully saturated or aromatic wherein the said cabocyclic ring or heterocyclic ring represented by R$^2$ is unsubstituted or substituted by 1 to 3 R$^3$s,
R$^3$ represents independently:
(1) a halogen atom,
(2) a trihalomethyl group,
(3) a hydroxy group,
(4) an alkyl group of 1 to 15 carbon atoms,
(5) an alkoxy group of 1 to 4 carbon atoms,
(6) an alkylthio, alkylsulfinyl or alkylsulfonyl group of 1 to 4 carbon atoms,
(7) a group of the formula:

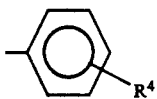

in which R$^4$ represents a hydrogen atom, a halogen atom, a trihalomethyl group, a hydroxy group, an alkyl group of 1 to 4 carbon atoms or an alkoxy group of 1 to 4 carbon atoms,
(8) a group of the formula

—NR$^5$R$^6$ in which R$^5$ and R$^6$ independently represent a hydrogen atom or an alkyl group of 1 ; to 4 carbon atoms,
(9) a group of the formula

—CO—R$^7$ in which R$^7$ represents an alkyl group of 1 to 4 carbon atoms or a phenyl group substituted by R$^4$ in which R$^4$ is as hereinbefore defined,
(10) a group of the formula:

—COOR$^8$ in which R$^8$ represents a hydrogen atom or an alkyl group of 1 to 4 carbon atoms,

(11) a group of the formula:

—CONR$^5$R$^6$ in which R$^5$ and R$^6$ are as hereinbefore defined,
(12) a group of the formula:

—SO$_2$NR$^5$R$^6$ in which R$^5$ and R$^6$ are as hereinbefore defined,
(13) a cyano group,
(14) a nitro group, or
(15) a group of the formula:

—NHCO—R$^7$, in which R$^7$ is as hereinbefore defined,
Z represents:
(1) a hydrogen atom,
(2) a group of the formula

—COR$^9$ in which R$^9$ represents an alkyl group of 1 to 4 carbon atoms or a phenyl group substituted by R$^{10}$, in which R$^{10}$ represents a hydrogen atom, a halogen atom, a trihalomethyl group, an alkyl group of 1 to 4 carbon atoms or an alkoxy group of 1 to 4 carbon atoms,
(3) a group of the formula:

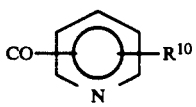

in which R$^{10}$ is as hereinbefore defined,
(4) a group of the formula:

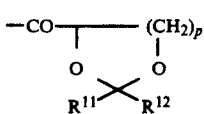

in which R$^{11}$ and R$^{12}$ independently represent a hydrogen atom, an alkyl group of 1 to 4 carbon atoms or a phenyl group substituted by R$^{10}$, in which R$^{10}$ is as hereinbefore defined, or R$^{11}$ and R$^{12}$ together represent an alkylene group of 4 or 5 carbon atoms and p is an integer of 1 or 2,
(5) a group of the formula:

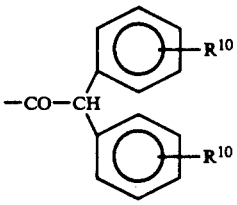

in which each of the two R$^{10}$s are independently as hereinbefore defined,
(6) a group of the formula:

$$-CO-(CH_2)_q-CONH-\underset{R^{10}}{\text{[fluorene-like tricyclic structure]}}$$

in which $R^{10}$ is as hereinbefore defined and q is an integer of 1 to 4, (7) a group of the formula:

$$\underset{O}{\overset{\text{[phthalide structure]}}{\|}}-R^{10}$$

in which $R^{10}$ is as hereinbefore defined,

Ⓐ represents a phenyl or cycloalkyl group of 4 to 7 carbon atoms, substituted by $R^{13}$, in which $R^{13}$ represents a hydrogen atom, a halogen atom, a trihalomethyl group, an alkyl group of 1 to 4 carbon atoms or an alkoxyl group of 1 to 4 carbon atoms, and m and n represent:
(1) when m is zero, n is an integer of 1 to 4, and
(2) when n is zero, m is an integer of 1 to 4, with the proviso that
  (i) when $R^1$ represents a hydrogen atom, $R^2$ represents a pyridyl group, m represents an integer of 2 and when n represents zero, Z does not represent a hydrogen atom, and
  (ii) when $R^2$ represents a heterocyclic ring selected from the group consisting of benzthiazole, thiazole, isothiazole, benzoxazole, oxazole and isoxazole wherein the said ring represented by $R^2$ is unsubstituted or substituted by 1 to 3 $R^3$s, where at least one of $R^3$ represents:
    (1) a group of the formula:

$$-NR^5R^6$$

in which $R^5$ and $R^6$ independently represent a hydrogen atom or an alkyl group of 1 to 4 carbon atoms,
    (2) a group of the formula:

$$-CONR^5R^6$$

in which $R^5$ and $R^6$ are as hereinbefore defined,
    (3) a group of the formula:

$$-SO_2NR^5R^6$$

in which $R^5$ and $R^6$ are as hereinbefore defined,
    (4) a cyano group,
    (5) a nitro group, or
    (6) a group of the formula:

$$-NHCO-R^7,$$

in which $R^7$ represents an alkyl group of 1 to 4 carbon atoms or a phenyl group substituted by a hydrogen atom, a halogen atom, a trihalomethyl group, a hydroxy group, an alkyl group of 1 to 4 carbon atoms, an alkoxyl group of 1 to 4 carbon atoms, Z does not represent a hydrogen atom, or a non-toxic salt thereof.

2. A compound according to claim 1, which is that of the formula:

$$Z-S\underset{CONH}{\overset{\text{Ⓐ}}{\diagdown}}\underset{CONH-R^2}{\overset{(CH_2)_m-COOR^1}{\diagup}} \quad (Ia)$$

(wherein the various symbols are as hereinbefore defined).

3. A compound according to claim 1, which is that of the formula:

$$Z-S\underset{CONH}{\overset{\text{Ⓐ}}{\diagdown}}\underset{COOR^1}{\overset{(CH_2)_n-CONH-R^2}{\diagup}} \quad (Ib)$$

(wherein the various symbols are as hereinbefore defined).

4. A compound according to claim 2, wherein Z represents a hydrogen atom.

5. A compound according to claim 2, wherein $R^2$ represents a carbocyclic ring unsubstituted or substituted by $R^3$.

6. A compound according to claim 2, wherein the carbocyclic ring is a benzene or naphthalene ring.

7. A compound according to claim 2, which is:
N-(3-mercapto-2-benzylpropionyl)-α-anilinoaspartic acid,
N-(3-mercapto-2-benzylpropionyl)-α-anilinoglutamic acid,
N-(3-mercapto-2-benzylpropionyl)-α-(4-chloroanilino)-glutamic acid,
N-(3-mercapto-2-benzylpropionyl)-α-(4-iodoanilino)-glutamic acid,
N-(3-mercapto-2-benzylpropionyl)-α-(4-methoxyanilino)glutamic acid, or
N-(3-mercapto-2-benzylpropionyl)-α-(4-acetylanilino)-glutamic acid, or β-methyl ester of the corresponding aspartic acid derivative, or a non-toxic salt of β-carboxylic acid or the corresponding aspartic acid derivative, or γ-methyl ester of the corresponding glutamic acid derivative, or a non-toxic salt of γ-carboxylic acid of the corresponding glutamic acid derivative.

8. A compound according to claim 2, wherein $R^2$ represents a heterocyclic ring selected from the group consisting of furan, thiophene, pyrrole, oxazole, isoxazole, thiazole, isothiazole, imidazole, pyrazole, furazan, pyran, pyridine, pyridazine, pyrimidine, pyrazine, indole, isoindole, benzofuran, benzothiophene, indolizine, benzimidazole, benzthiazole, benzoxazole, chromene, quinoline, isoquinoline, quinolizine, purine, indazole, quinazoline, cinnoline, quinoxaline, phthalazine, pteridine, benzodiazepine, carbazole, acridine, phenanthridine, xanthene, phenazine and phenothiazine rings with the proviso that
  (i) when $R^1$ represents a hydrogen atom, $R^2$ represents a pyridyl group, m represents an integer of 2 and when n represents zero, Z does not represent a hydrogen atom, and (ii) when $R^2$ represents a heterocyclic ring selected from the group consisting of thiazole, isothiazole, oxazole, isoxazole, benzthiazole and benzoxazole, wherein the said ring represented by $R^2$ is unsubstituted or substituted by 1 to 3 $R^3$s, where at least one of $R^3$ represents:

(1) a group of the formula:

—$NR^5R^6$ in which $R^5$ and $R^6$ independently represent a hydrogen atom or an alkyl group of 1 to 4 carbon atoms, (2) a group of the formula:

—$CONR^5R^6$ in which $R^5$ and $R^6$ are as hereinbefore defined,
(3) a group of the formula:

—$SO_2NR^5R^6$ in which $R^5$ and $R^6$ are as hereinbefore defined,
(4) a cyano group, or
(5) a nitro group, or
(6) a group of the formula:

—NHCO—$R^7$, in which $R^7$ represents an alkyl group of 1 to 4 carbon atoms or a phenyl group substituted by a hydrogen atom, a halogen atom, a trihalomethyl group, a hydroxy group, an alkyl group of 1 to 4 carbon atoms, an alkoxyl group of 1 to 4 carbon atoms, Z does not represent a hydrogen atom.

9. A compound according to claim 2, wherein the heterocyclic ring represented by $R^2$ is pyrrole, imidazole, pyrazole, pyridine, pyridazine, pyrimidine, pyrazine, indole, isoindole, indolizine, benzimidazole, quinoline, isoquinoline, quinolizine, indazole, quinazoline, cinnoline, quinoxaline, phthalazine, or benzodiazepine ring, with the proviso that when $R^1$ represents a hydrogen atom, $R^2$ represents a 4-pyridyl group, m represents an integer of 2 and when n represents zero, Z does not represent a hydrogen atom.

10. A compound according to claim 2, wherein the heterocyclic ring represented by $R^2$ is furan thiophene, pyridine, pyrimidine, pyrazine, benzimidazole, benzthiazole, benzoxazole or benzodiazepine with the proviso that (i) when $R^1$ represents a hydrogen atom, $R^2$ represents a pyridyl group, m represents an integer of 2 and when n represents zero, Z does not represent a hydrogen atom, and (ii) when $R^2$ represents a heterocyclic ring selected from the group consisting of benzthiazole and benzoxazole, wherein the said ring represented by $R^2$ is unsubstituted or substituted by 1 to 3 $R^3$s, where at least one of $R^3$ represents:

(1) a group of the formula:

—$NR^5R^6$ in which $R^5$ and $R^6$ independently represent a hydrogen atom or an alkyl group of 1 to 4 carbon atoms, (2) a group of the formula:

—$CONR^5R^6$ in which $R^5$ and $R^6$ are as hereinbefore defined,
(3) a group of the formula:

—$SO_2NR^5R^6$ in which $R^5$ and $R^6$ are as hereinbefore defined,
(4) a cyano group,
(5) a nitro group, or
(6) a group of the formula:

—NHCO—$R^7$, in which $R^7$ represents an alkyl group of 1 to 4 carbon atoms or a phenyl group substituted by a hydrogen atom, a halogen atom, a trihalomethyl group, a hydroxy group, an alkyl group of 1 to 4 carbon atoms, an alkoxyl group of 1 to 4 carbon atoms, .

Z does not represent a hydrogen atom.

11. A compound according to claim 2, which is: N-(3-mercapto-2-benzylpropionyl)glutamic acid α-(2,3-dihydro-1-methyl-5-phenyl-1H-1,4-benzodiazepin-7-yl)amide, or γ-methyl ester of the corresponding glutamic acid derivative, or a non-toxic salt of γ-carboxylic acid of the corresponding glutamic acid derivative.

12. A compound according to claim 3, wherein Z represents a hydrogen atom.

13. A compound according to claim 3, wherein $R^2$ represents a carbocyclic ring unsubstituted or substituted by $R^3$.

14. A compound according to claim 3, which is:
N-(3-mercapto-2-benzylpropionyl)-γ-anilinoglutamic acid,
N-(3-mercapto-2-benzylpropionyl)-β-anilinoaspartic acid,
N-(3-mercapto-2-benzylpropionyl)-β-(4-iodonilino)aspartic acid or
N-(3-mercapto-2-benzylpropionyl)-β- (4-methoxyanilino)aspartic acid, or α-methyl ester of the corresponding aspartic or glutamic acid derivative, or a non-toxic salt of α-carboxylic acid of the corresponding aspartic or glutamic acid derivative.

15. A compound according to claim 3, wherein $R^2$ represents a heterocyclic ring unsubstituted or substituted by $R^3$.

16. A compound according to claim 3, which is N-(3-mercapto-2-benzylpropionyl)aspartic acid β-(2,3-dihydro-1-methyl-5-phenyl-1H-1,4-benzodiazepin-7-yl)amide, or α-methyl ester of the corresponding aspartic acid derivative, or a non-toxic salt of α-carboxylic acid of the corresponding aspartic acid derivative.

17. A compound according to claim 2, wherein Z represents a group other than a hydrogen atom.

18. A compound according to claim 2, which is:
N-(3-benzoylthio-2-benzylpropionyl)-α-anilino glutamic acid,
N-(3-nicotinoylthio-2-benzylpropionyl)-α-anilino glutamic acid,
N-(3-diphenylacetylthio-2-benzylpropionyl)-α-anilinoglutamic acid,
N-[3-(2,2-dimethyl-1,3-dioxolan-4-carbonyl)thio-2-benzylpropionyl]-α-anilinoglutamic acid,
N-[3-[N-(9-fluorenyl)succinamoyl]thio-2-benzylpropionyl]-α-anilinoglutamic acid,
N-[3-(phthalid-3-yl)thio-2-benzylpropionyl]-α-anilinoglutamic acid, N-[3-(phthalid-3-yl)thio-2-benzylpropionyl]-glutamic acid α-(2-benzthiazolyl)amide, or N-[3-(phthalid-3-yl)thio-2-benzylpropionyl]-α-anilinoaspartic acid, or γ-methyl ester of the corresponding glutamic acid derivative, or a non-toxic salt of γ-carboxylic acid of the corresponding glutamic acid derivative.

19. A compound according to claim 3, wherein Z represents a group other than a hydrogen atom.

20. A compound according to claim 3, which is N-(3-acetylthio-2-benzylpropionyl)-γ-anilino-glutamic acid or N-(3-nicotinoylthio-2-benzylpropionyl)-β-anilinoaspartic acid, or α-methyl ester of the corresponding aspartic or glutamic acid derivative, or a non-toxic salt of α-carboxylic acid of the corresponding aspartic or glutamic acid derivative.

21. A pharmaceutical composition for the prevention and treatment of pain, anxiety or convulsion, which comprises, as active ingredient, an effective amount of an amino acid compound of the formula:

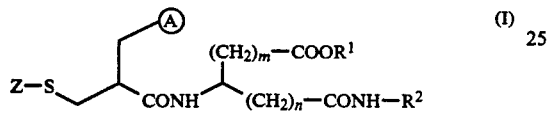
(I)

(wherein the various symbols are as defined in claim 1) or a non-toxic salt thereof and a pharmaceutically acceptable carrier.

22. A method for the prevention and treatment of pain, anxiety or convulsion, which comprises the administration of an effective amount of an amino acid compound of the formula:

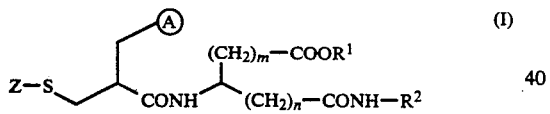
(I)

(wherein the various symbols are as defined in claim 1) or a non-toxic salt thereof and a pharmaceutically acceptable carrier.

23. A compound according to claim 1, wherein the heterocyclic ring represented by $R^2$ is pyrrole, imidazole, pyrazole, pyridine, pyridaxine, pyrimidine, pyrazine, indole, isoindole, indolizine, benzimidazole, quinoline, isoquinoline, quinolizine, indazole, quinazoline, cinnoline, quinoxaline, phthalazine, benzodiazepine, carbazole, acridine, phenanthridine or phenazine ring with the proviso that when $R^1$ represents a hydrogen atom, $R^2$ represents a pyridyl group, m represents an integer of 2 and when n represents zero, Z does not represent a hydrogen atom.

24. A compound according to claim 1, wherein the heterocyclic ring represented by $R^2$ is pyridazine, pyrimidine, pyrazine, quinoline, isoquinoline, quinolizine, quinazoline, cinnoline, quinoxaline, phthalazine, acridine, phenanthridine or phenazine ring.

25. A compound according to claim 24, wherein Z represents a hydrogen atom.

26. A compound according to claim 24, wherein Z represents a hydrogen atom and $R^2$ represents pyridazine, pyrimidine, pyrazine, quinazoline, cinnoline, quinoxaline phthalazine and phenazine ring, which may be partially or fully saturated or aromatic wherein the substituent represented by $R^2$ is unsubstituted or substituted by 1 to 3 $R^3$s, one of the $R^3$s represents (1) a group of the formula:

in which $R^5$ and $R^6$ independently represent a hydrogen atom or an alkyl group of 1 to 4 carbon atoms, (2) a group of the formula:

in which $R^5$ and $R^6$ are as hereinbefore defined, (3) a group of the formula:

in which $R^5$ and $R^6$ are as hereinbefore defined, (4) a cyano group,
(5) a nitro group, or
(6) a group of the formula:

in which $R^7$ represents an alkyl group of 1 to 4 carbon atoms or a phenyl group substituted by a hydrogen atom, a halogen atom, a trihalomethyl group, a hydroxy group, an alkyl group of 1 to 4 carbon atoms, an alkoxyl group of 1 to 4 carbon atoms, and the other $R^3$s represent independently:

(1) a halogen atom,
(2) a trihalomethyl group,
(3) a hydroxy group,
(4) an alkyl group of 1 to 15 carbon atoms,
(5) an alkoxy group of 1 to 4 carbon atoms,
(6) an alkylthio, alkylsulfinyl or alkylsulfonyl group of 1 to 4 carbon atoms,
(7) a group of the formula

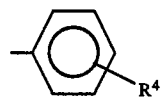

in which $R^4$ represents a hydrogen atom, a halogen atom, a trihalomethyl group, a hydroxy group, an alkyl group of 1 to 4 carbon atoms or an alkoxy group of 1 to 4 carbon atoms, (8) a group of the formula:

in which $R^5$ and $R^6$ independently represent a hydrogen atom or an alkyl group of 1 to 4 carbon atoms, (9) a group of the formula:

in which $R^7$ is as hereinbefore defined,
(10) a group of the formula:

in which $R^8$ represents a hydrogen atom or an alkyl group of 1 to 4 carbon atoms,

(11) a group of the formula:

—CONR$^5$R$^6$ in which R$^5$ and R$^6$ are as hereinbefore defined,
(12) a group of the formula:

—SO$_2$NR$^5$R$^6$ in which R$^5$ and R$^6$ are as hereinbefore defined,
(13) a cyano group,
(14) a nitro group, or
(15) a group of the formula:

—NHCO—R$^7$, in which R$^7$ is as hereinbefore defined.

27. A compound according to claim 26, wherein the heterocyclic ring represented by R$^2$ is pyrazine or pyrimidine.

28. A compound according to claim 27, which is N-(3-mercapto-2RS-benzylpropionyl)-L-glutamic acid α-(pyrazin-2-yl)amide, or
N-(3-mercapto-2RS-benzylpropionyl)-L-glutamic acid α-(pyrimidin-2-yl)amide, or
non-toxic salt of γ-carboxylic acid of the corresponding glutamic acid derivative.

* * * * *